(12) United States Patent
Hong et al.

(10) Patent No.: US 8,153,122 B2
(45) Date of Patent: Apr. 10, 2012

(54) PHARMACEUTICAL COMPOSITION FOR TREATING CHOLANGIOCARCINOMA, A METHOD FOR INHIBITING GROWTH OR INVASION OF CHOLANGIOCARCINOMA AND A METHOD FOR TREATING CHOLANGIOCARCINOMA

(75) Inventors: Hyo Jeong Hong, Daejeon (KR); Jung-Whoi Lee, Seoul (KR); Jin Man Kim, Daejeon (KR); Yeon Sung Son, Seoul (KR); Eung Suck Lee, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 262 days.

(21) Appl. No.: 12/438,354

(22) PCT Filed: Aug. 23, 2007

(86) PCT No.: PCT/KR2007/004046
§ 371 (c)(1),
(2), (4) Date: Apr. 1, 2009

(87) PCT Pub. No.: WO2008/023947
PCT Pub. Date: Feb. 28, 2008

(65) Prior Publication Data
US 2010/0196350 A1 Aug. 5, 2010

(30) Foreign Application Priority Data

Aug. 23, 2006 (KR) .................. 10-2006-0079969
Aug. 23, 2007 (KR) .................. 10-2007-0084868

(51) Int. Cl.
*A61K 39/395* (2006.01)
(52) U.S. Cl. .................... 424/130.1; 424/141.1
(58) Field of Classification Search .................. None
See application file for complete search history.

(56) References Cited

U.S. PATENT DOCUMENTS

| 5,872,225 A | 2/1999 | Lemmon |
| 2004/0115206 A1 | 6/2004 | Primiano et al. |
| 2004/0259084 A1 | 12/2004 | Altevogt et al. |

FOREIGN PATENT DOCUMENTS

| EP | 1172654 A1 | 1/2002 |
| EP | 1671645 A1 | 6/2006 |
| WO | 2004/037198 A2 | 5/2004 |
| WO | 2006/013051 A1 | 2/2006 |

OTHER PUBLICATIONS

Rudikoff et al, Proc. Natl. Acad. Sci. USA, 79(6):1979-1983, Mar. 1982.*
Colman P. M, Research in Immunology, 145:33-36, 1994.*
MacCallum et al J. Mol. Biol., 262, 732-745, 1996, IDS.*
Anderson et al., "Diagnosis and treatment of cholangiocarcinoma," The Oncologist 2004, vol. 9, No. 1, 2004, pp. 43-57.
Arlt et al., "Efficient inhibition of intra-peritoneal tumor growth and dissemination of human ovarian carcinoma cells in nude mice by anti-L1-cell adhesion molecule monoclonal antibody treatment," Cancer Research, vol. 66, No. 2, Jan. 1, 2006, pp. 936-943, American Association for Cancer Research, Baltimore, MD, US.
De Boer, C.J. et al., "Expression of Ep-CAM in normal, regenerating, metaplastic, and neoplastic liver," The Journal of Pathology, Jun. 1999, vol. 188, No. 2, pp. 201-206.
European Search Report dated Feb. 8, 2010, for EP Application No. 07 79 3649.
Huszar et al., "Expression profile analysis in multiple human tumors identifies L1 (CD171) as a molecular marker for differential diagnosis and targeted therapy," Human Pathology, vol. 37, No. 8, Aug. 1, 2006, pp. 1000-1008, Saunders, Philadelphia, PA, US.
Ieta et al., "CEACAM6 gene expression in intrahepatic choloangiocarcinoma," British Journal of Cancer, vol. 95, No. 4, Aug. 2006, pp. 532-540.
Li et al., "L1 cell adhesion molecule is a novel independent poor prognostic factor of extrahepatic cholangiocarcinoma," Clinical Cancer Research, vol. 15, No. 23, Dec. 2009, pp. 7345-7351.
Sell et al., "Evidence for the stem cell origin of hepatocellular carcinoma and cholangiocarcinoma," The American Journal of Pathology, vol. 134, No. 6, Jun. 1989, pp. 1347-1363.
Pederson et al., "Molecular chemotherapy combined with radiation therapy enhances killing of cholangiocarcinoma cells in Vitro and in Vivo," Cancer Research 57, Oct. 1, 1997, pp. 4325-4332.
Roberts et al., "The Pathobiology of Biliary Epithelia," Gastroenterology, 1997, vol. 112, pp. 269-279.
Yamaguchi et al., "Establishment and characterization of the human cholangiocarcinoma cell line HChol-Y1 in a serum-free, chemically defined medium," Journal of the National Cancer Institute, Jul. 1985, vol. 75, No. 1, pp. 29-35.
Ding et al., "Loss of constitutional heterozygosity on chromosomes 5 and 17 in cholangiocarcinoma," British Journal of Cancer, May 1993, vol. 67, pp. 1007-1010.

(Continued)

*Primary Examiner* — Misook Yu
*Assistant Examiner* — Mark Halvorson
(74) *Attorney, Agent, or Firm* — Knobbe, Martens, Olson & Bear, LLP

(57) ABSTRACT

Disclosed herein are a pharmaceutical composition for inhibiting the growth or metastasis of cholangiocarcinoma, comprising a L1CAM activity inhibitor or expression suppressor and a treatment method using the composition. This is based on the finding that L1CAM is overexpressed on cholangiocarcinoma and plays an important role in the growth and metastasis of cholangiocarcinoma and the mortality of cholangiocarcinoma patients increases as the expression rate of L1CAM increases. Also, antibodies inhibitory of the activity of L1CAM, or siRNAs suppressing the expression of L1CAM, are found to reduce the growth and invasion of cholangiocarcinoma cells. Mouse monoclonal antibodies, recognizing the L1CAM protein on the cholangiocarcinoma cell surface and binding specifically to cholangiocarcinoma tissues, or siRNAs, antisense oligonucleotides or shRNAs, may be useful in the treatment of cholangiocarcinoma by inhibiting the growth, invasion and migration of cholangiocarcinoma cell.

4 Claims, 11 Drawing Sheets

OTHER PUBLICATIONS

Kim et al., "Establishment and characterization of chromosomal aberrations in human cholangiocarcinoma cell lines by cross-species color banding," Genes, Chromosomes & Cancer, 2001, vol. 30, pp. 48-56, Wiley-Liss, Inc.

Modjtahedi, H. et al., "The receptor for EGF and its ligands: expression, prognostic value and target for therapy in cancer (Review)," International Journal of Oncology, 1994, vol. 4, pp. 277-296.

Nicholson, R.I. et al., "EGFR and cancer prognosis," European Journal of Cancer, vol. 37, 2001, pp. S9-S15.

Dassonville, O. et al., "EGFR targeting therapies: monoclonal antibodies versus tyrosine kinase inhibitors similarities and differences," Critical Reviews in Oncology/Hematology, vol. 62, 2007, pp. 53-61.

Bateman, et al., "Outline structure of the human L1 cell adhesion molecule and the sites where mutations cause neurological disorders," The EMBO Journal, vol. 15, No. 22, 1996, pp. 6050-6059, Oxford University Press.

Hlavin, M.L. et al., "Molecular structure and functional testing of human L1CAM: An interspecies comparison," Genomics, vol. 11, 1991, pp. 416-423, Academic Press, Inc.

Takeda et al., "A nonneuronal isoform of cell adhesion molecule L1: Tissue-specific expression and functional analysis," Journal of Neurochemistry, vol. 66, No. 6, 1996, pp. 2338-2349.

Thies et al., "Overexpression of the cell adhesion molecule L1 is associated with metastasis in cutaneous malignant melanoma," European Journal of Cancer, vol. 38, 2002, pp. 1708-1716.

Gutwein et al., "ADAM10-mediated cleavage of L1 adhesion molecule at the cell surface and in released membrane vesicles," The FASEB Journal, vol. 17(2), Feb. 2003, pp. 292-294.

Primiano et al., "Identification of potential anticancer drug targets through the selection of growth-inhibitory genetic suppressor elements," Cancer Cell., vol. 4(1), Jul. 2003, pp. 41-53, Cell Press.

Gavert et al., "L1, a novel target of -catenin signaling, transforms cells and is expressed at the invasive front of colon cancers," The Journal of Cell Biology, vol. 168(4), Feb. 14, 2005, pp. 633-642, The Rockefeller University Press.

Sui G. et al., "A DNA vector-based RNAi technology to suppress gene expression in mammalian cells," Proceedings of the National Academy of Sciences of the USA, Apr. 16, 2002, vol. 99, No. 8, pp. 5515-5520.

Brummelkamp et al., "A system for stable expression of short interfering RNAs in mammalian cells," Science, Apr. 19, 2002, vol. 296, pp. 550-553.

International Search Report issued for PCT/KR2007/004046 dated Nov. 22, 2007.

* cited by examiner

[Figure 1]
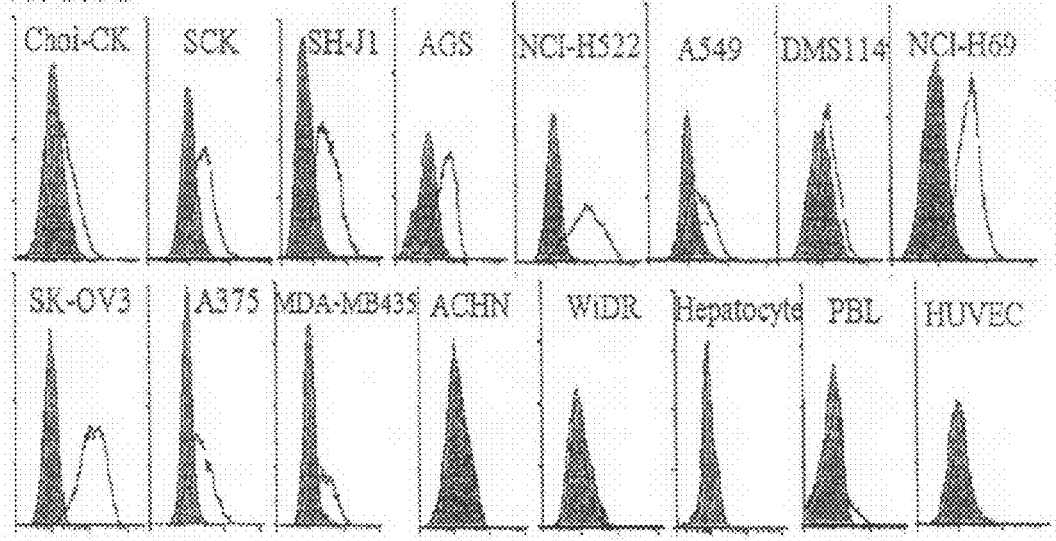
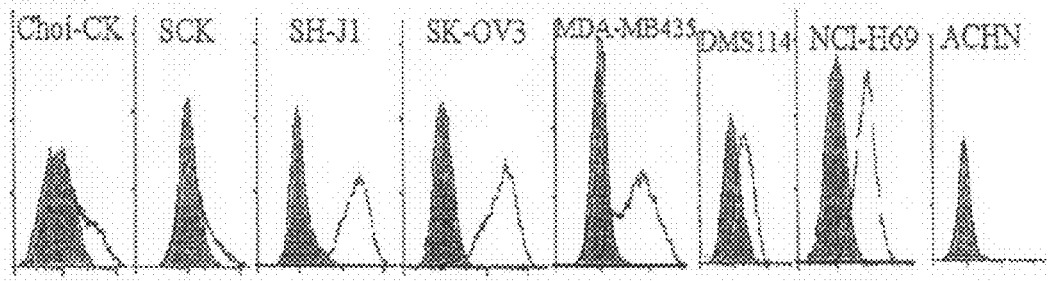
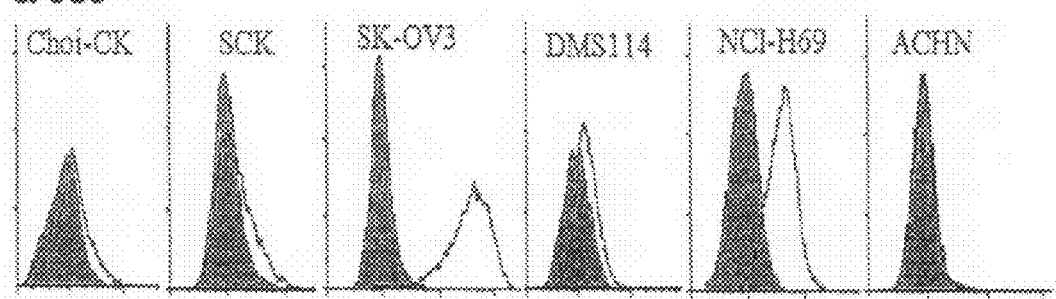
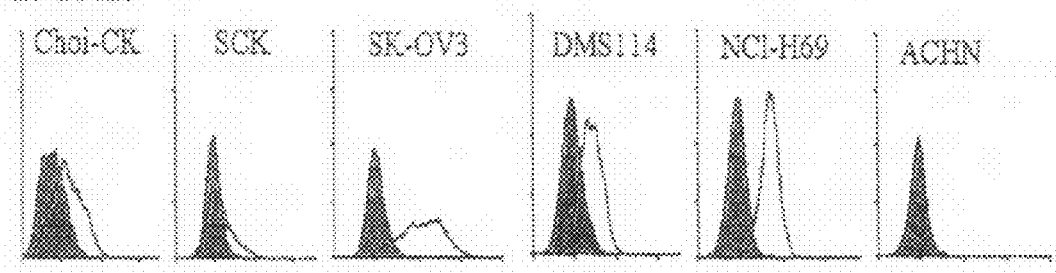

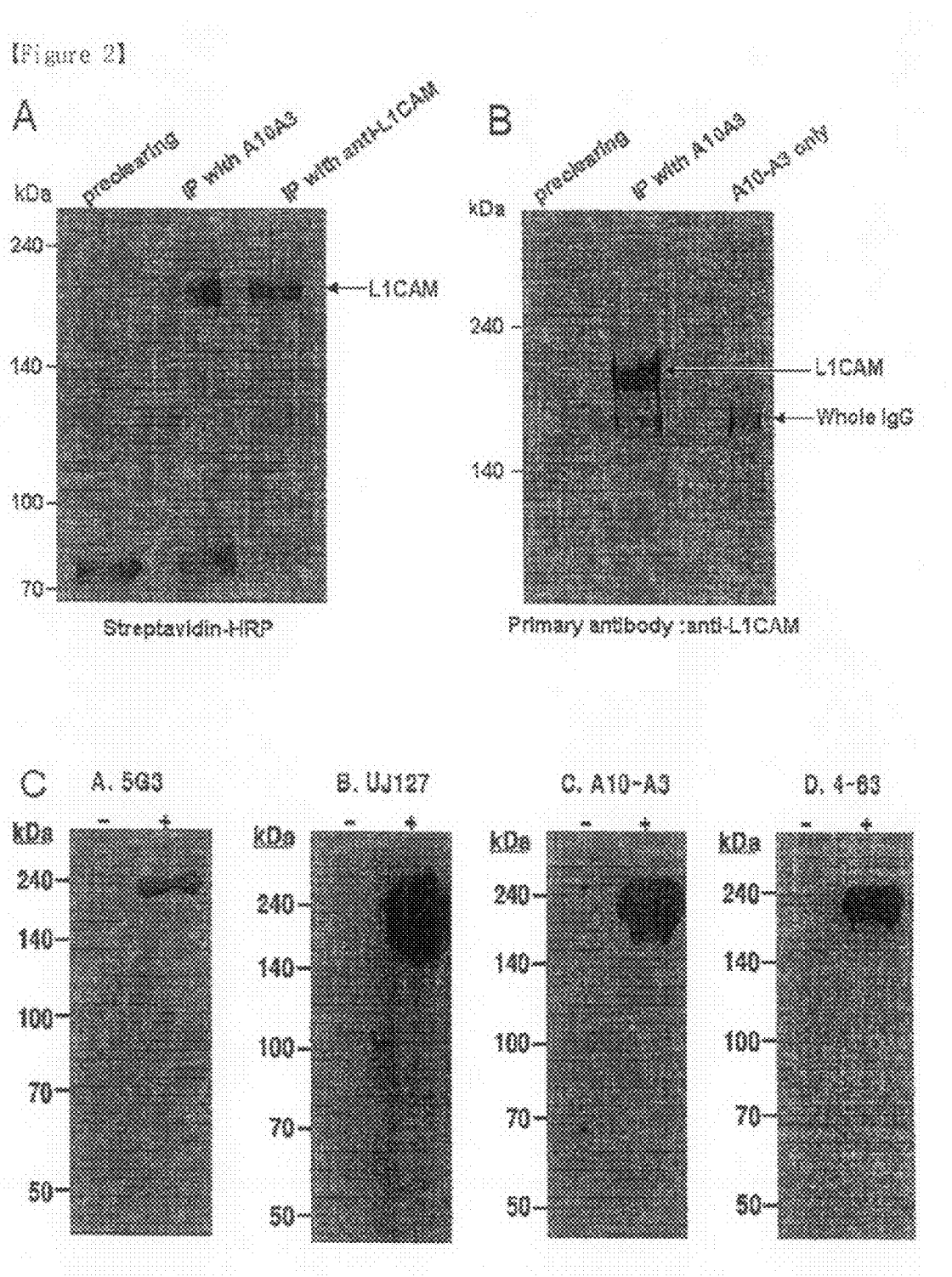

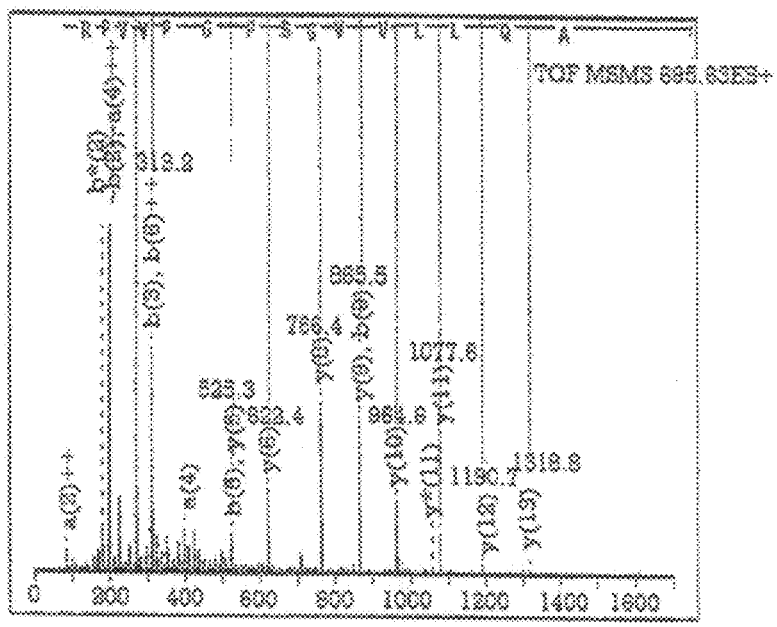
[Figure 3]

[Figure 4]
A. A10-A3
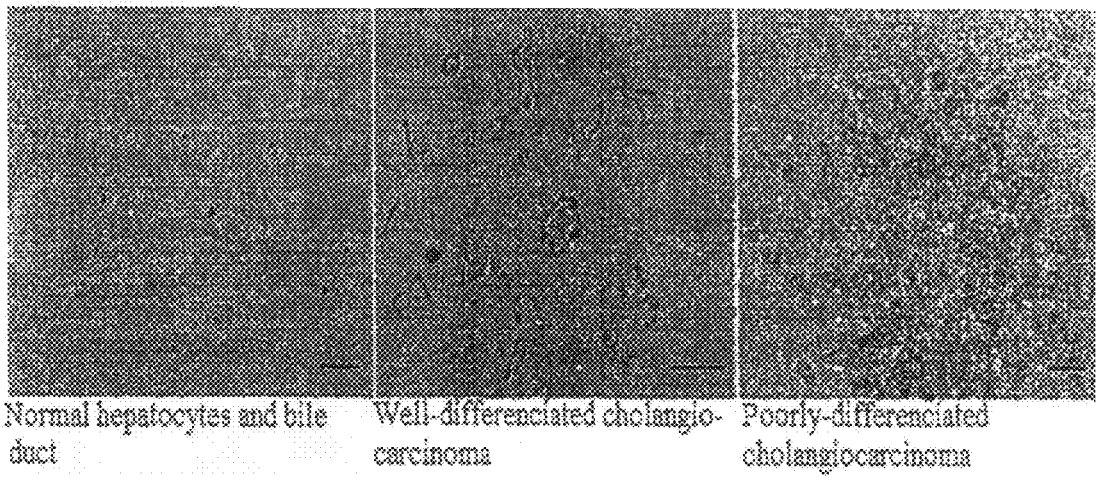
Normal hepatocytes and bile duct | Well-differentiated cholangio-carcinoma | Poorly-differenciated cholangiocarcinoma
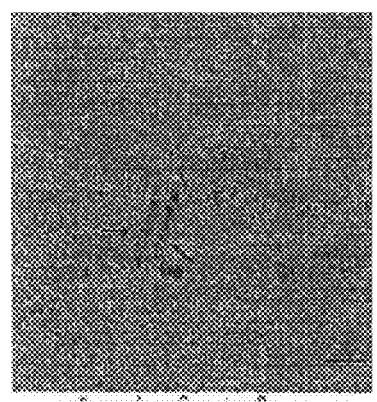
Invasive front of cholangiocarcinoma
B. 4-63
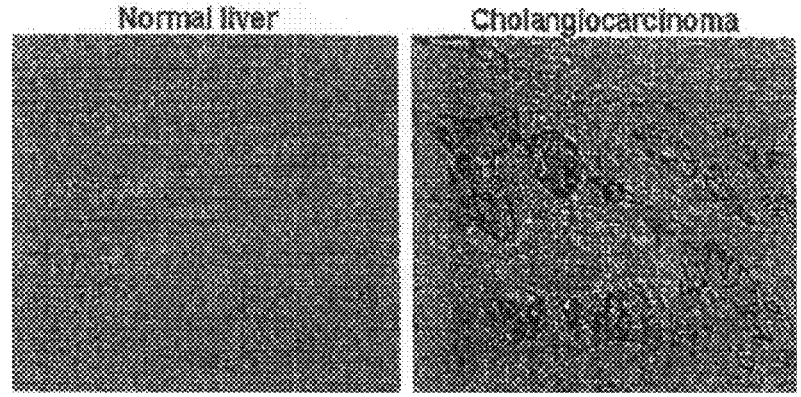

[Figure 5]

A. Correlation between L1 expression and clinicopathological properties in 42 cases of intrahepatic cholangiocarcinoma

| Category | L1 LEG n(%) | L1 HEG n(%) | P |
|---|---|---|---|
| Age (y) | | | |
| <62 | 10(53) | 9(47) | 1.000 |
| ≥62 | 13(57) | 10(43) | |
| Gender | | | |
| Men | 15(54) | 13(46) | 1.000 |
| Women | 8(57) | 6(43) | |
| Histologic grading | | | |
| G1 | 10(71) | 4(29) | 0.308 |
| G2 | 7(47) | 8(53) | |
| G3 | 6(46) | 7(54) | |
| Pathologic T stage | | | |
| T1, T2 | 14(64) | 8(36) | 0.352 |
| T3, T4 | 9(45) | 11(55) | |
| Venous/lymphatic invasion | | | |
| Negative | 20(56) | 16(44) | 1.000 |
| Positive | 3(50) | 3(50) | |
| Perineural invasion | | | |
| Negative | 16(56) | 11(44) | 0.525 |
| Positive | 7(47) | 8(53) | |

B. Correlation between L1 expression and clinicopathological properties in 103 cases of extrahepatic cholangiocarcinoma

| Category | L1 LEG n(%) | L1 HEG n(%) | P |
|---|---|---|---|
| Age (y) | | | |
| <66 | 26(58) | 19(42) | 0.689 |
| ≥66 | 36(62) | 22(38) | |
| Gender | | | |
| Men | 44(56) | 35(43) | 0.102 |
| Women | 18(75) | 6(25) | |
| Histologic grading | | | |
| G1 | 17(74) | 6(26) | 0.070 |
| G2 | 36(62) | 22(38) | |
| G3 | 9(41) | 13(69) | |
| Pathologic T stage | | | |
| T1, T2 | 36(62) | 22(38) | 0.689 |
| T3, T4 | 26(58) | 19(42) | |
| Venous/lymphatic invasion | | | |
| Negative | 34(58) | 25(42) | 0.660 |
| Positive | 28(64) | 16(36) | |
| Perineural invasion | | | |
| Negative | 26(70) | 11(30) | 0.144 |
| Positive | 36(54) | 30(46) | |

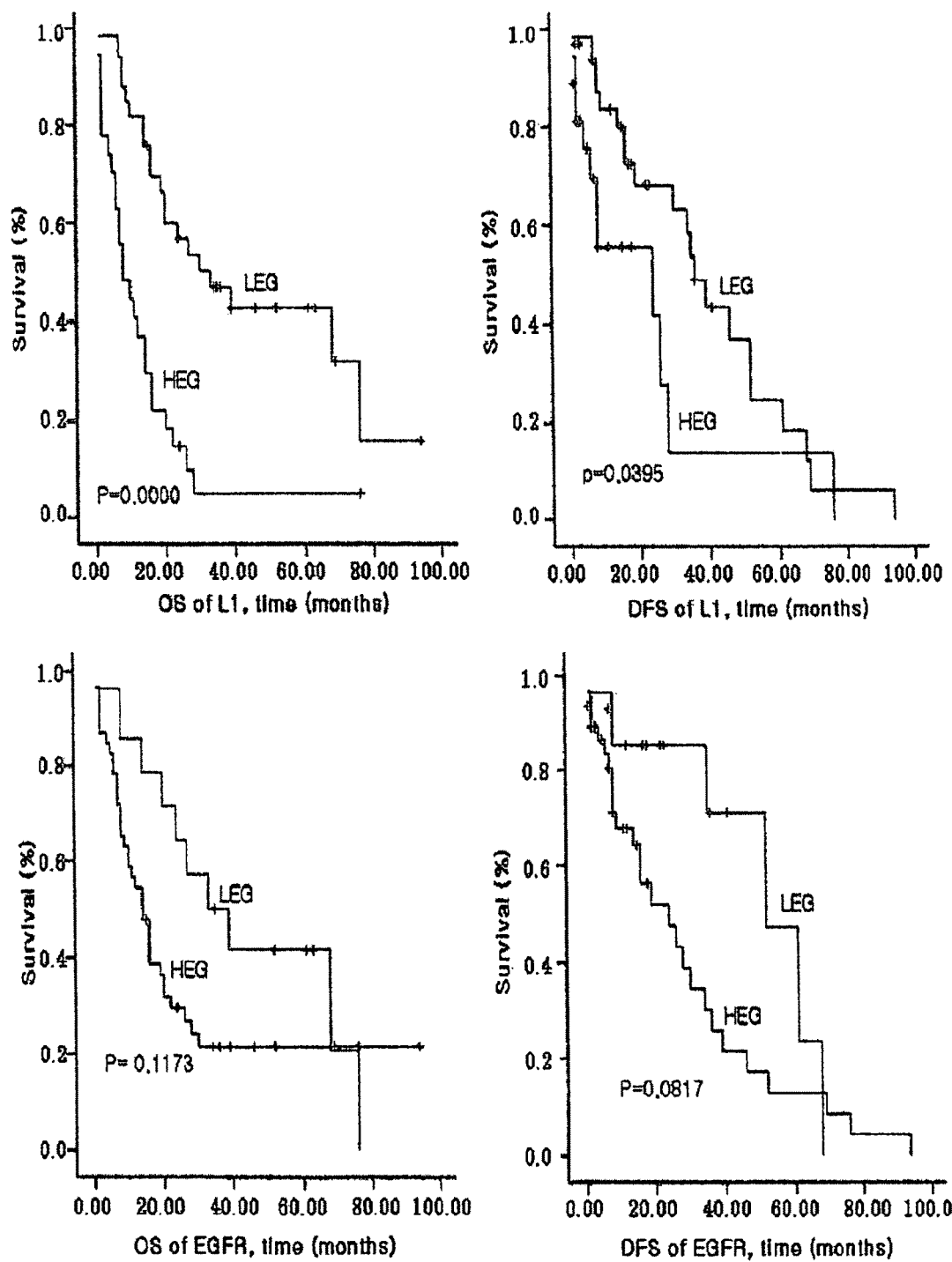
[Figure 6]

[Figure 7]
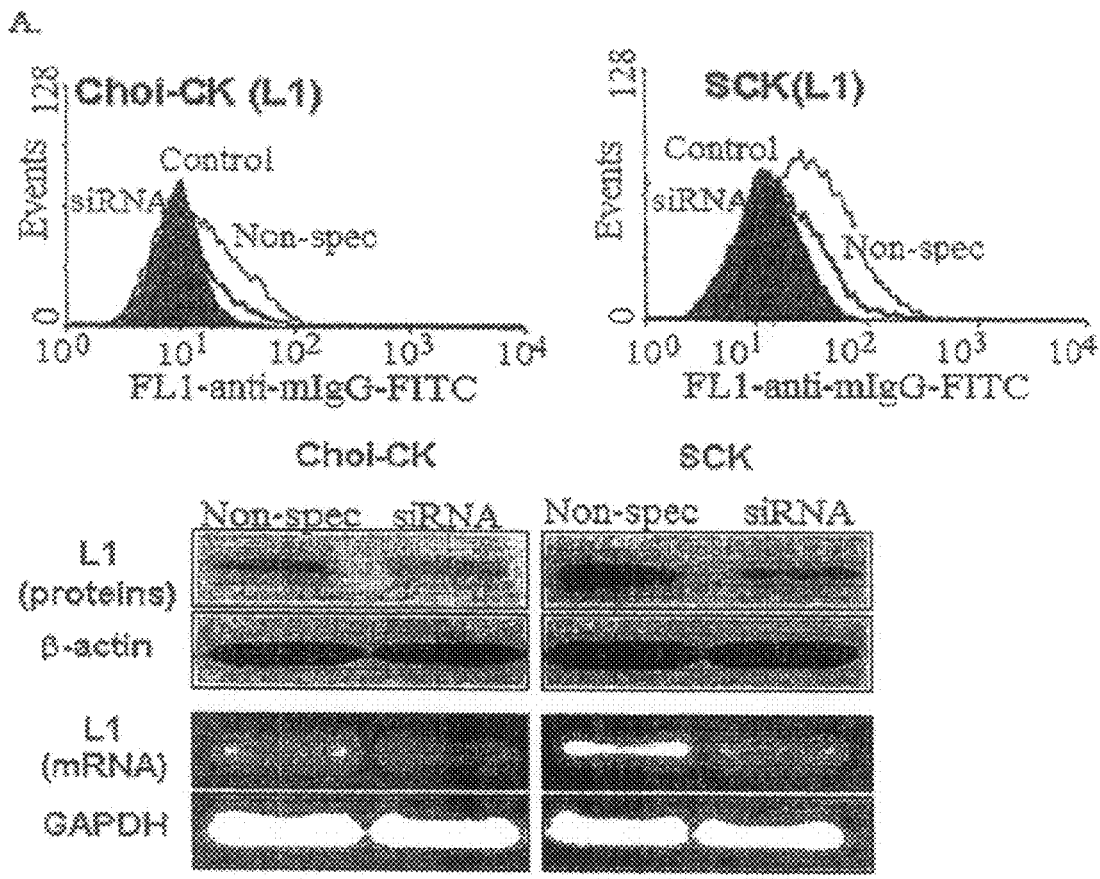
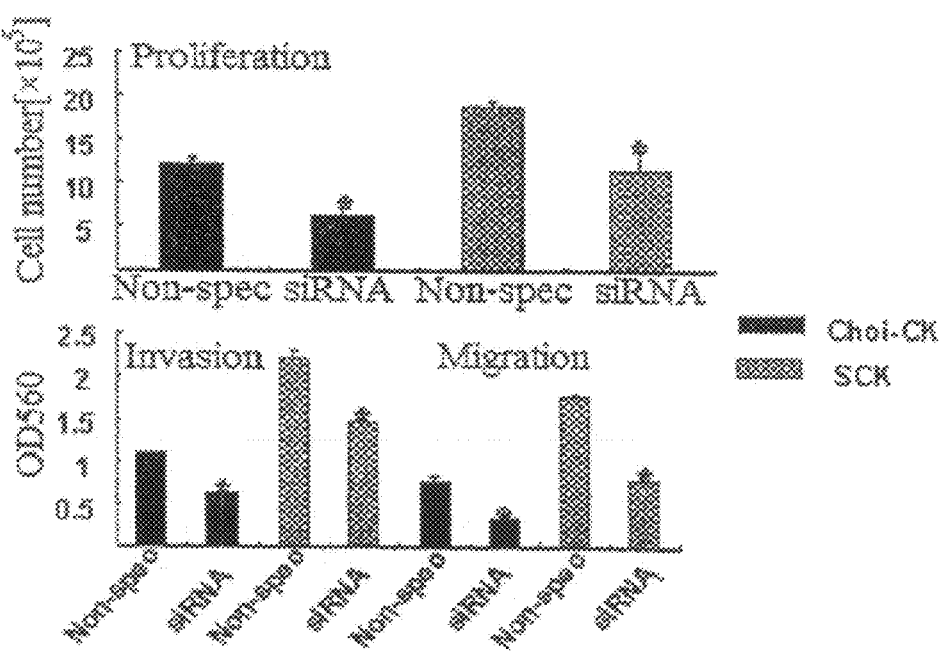

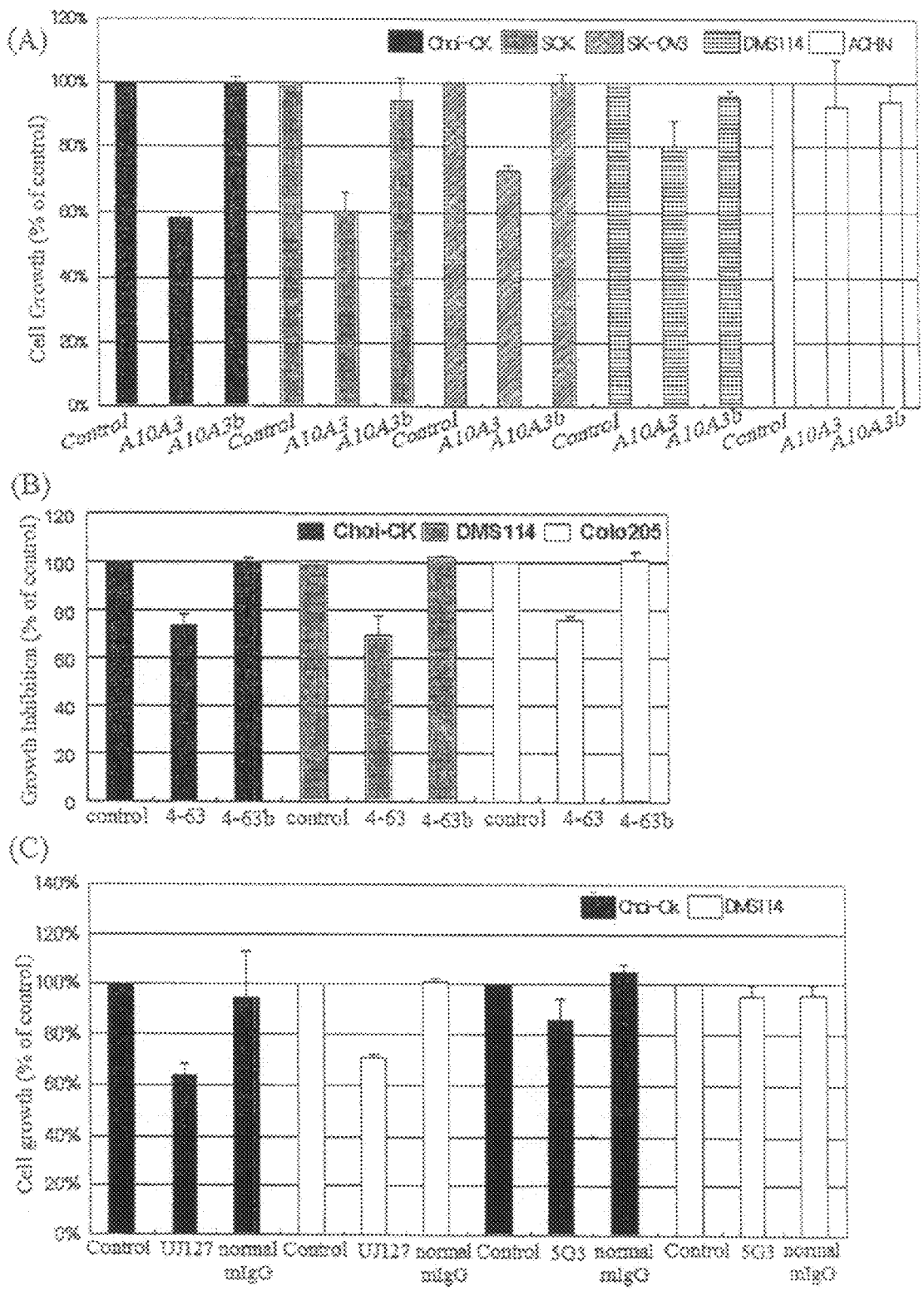
[Figure 8]

[Figure 9]
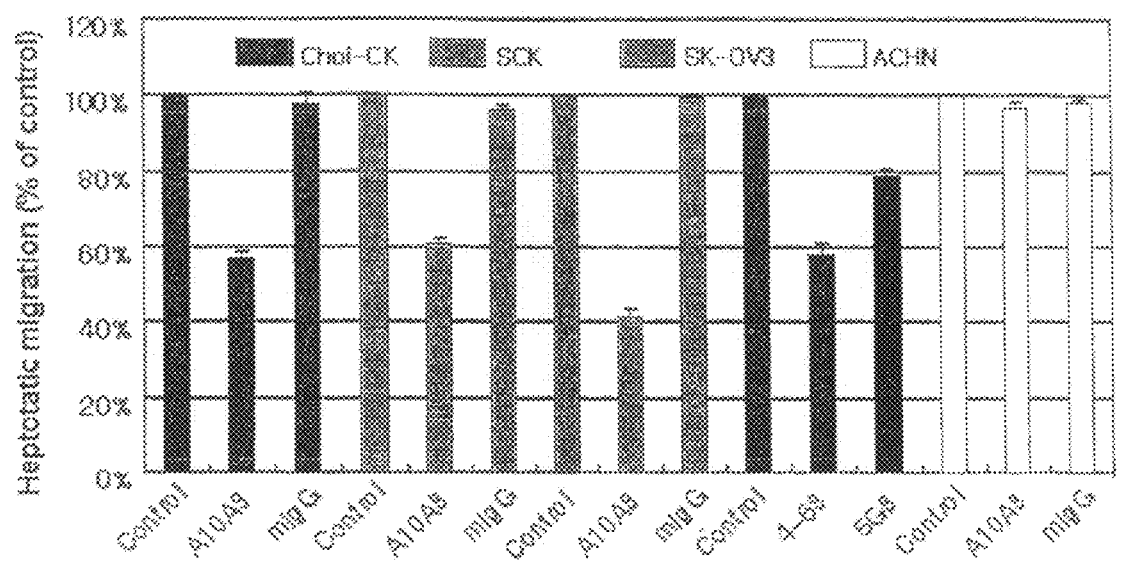
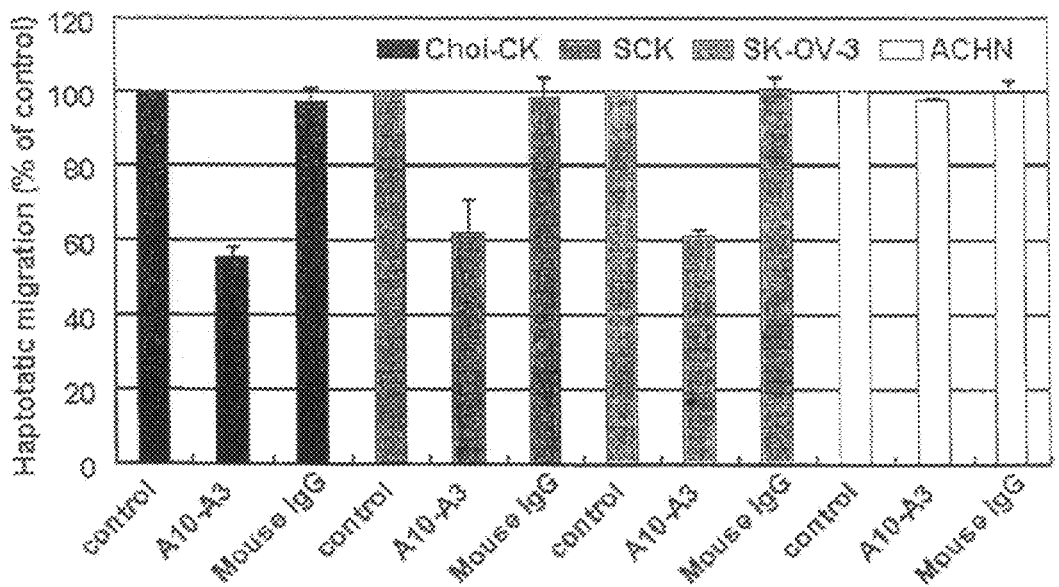

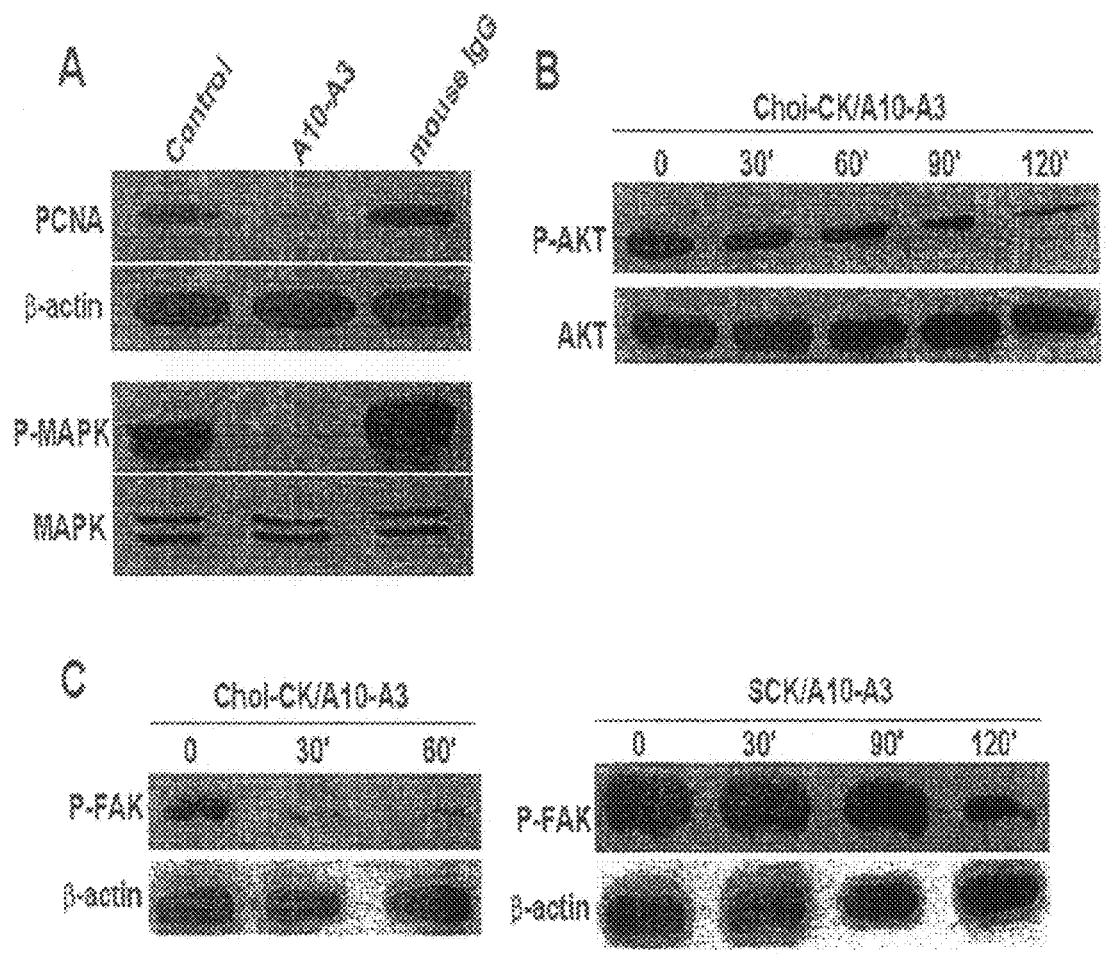
[Figure 10]

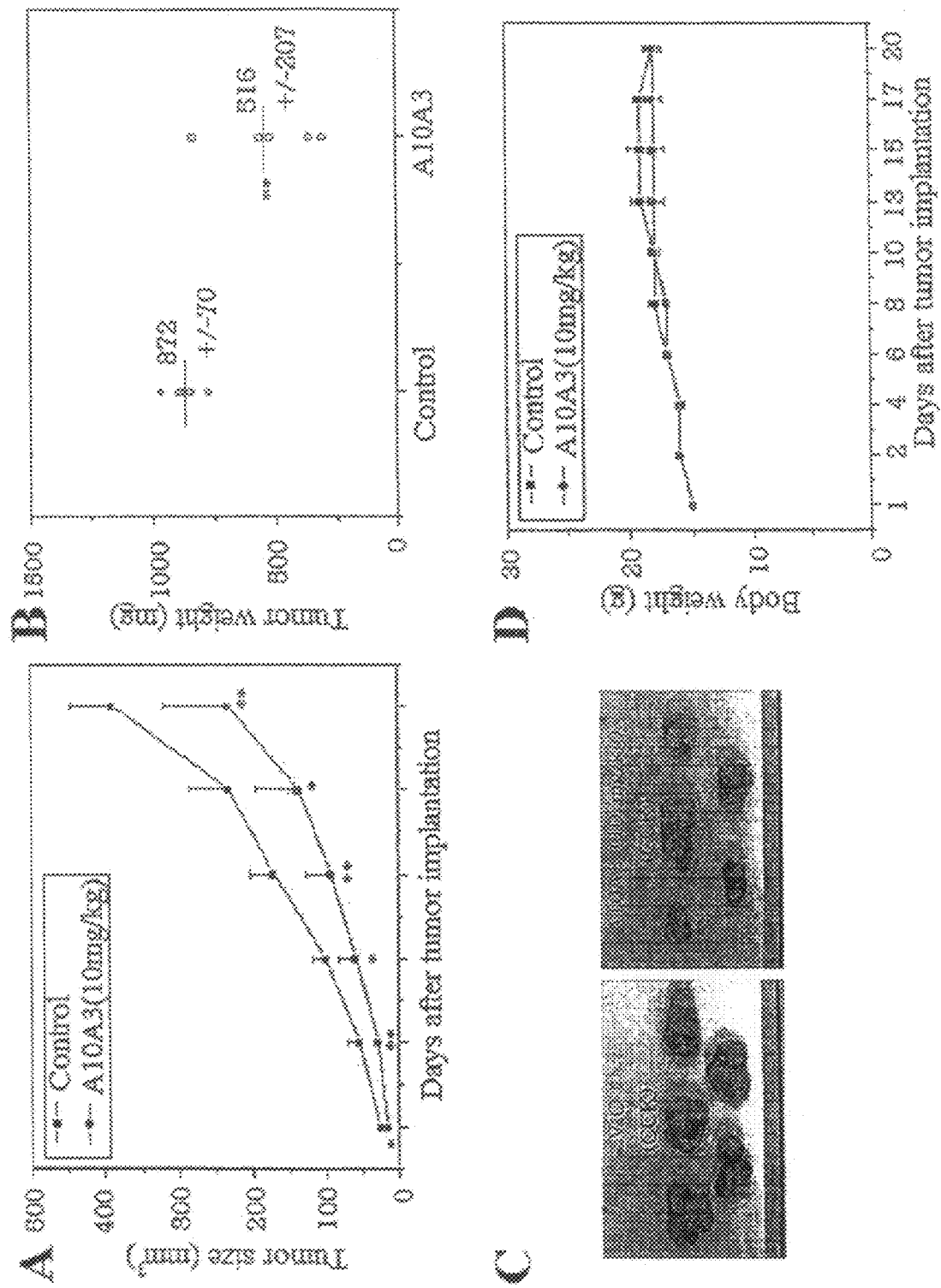
[Figure 11]

PHARMACEUTICAL COMPOSITION FOR TREATING CHOLANGIOCARCINOMA, A METHOD FOR INHIBITING GROWTH OR INVASION OF CHOLANGIOCARCINOMA AND A METHOD FOR TREATING CHOLANGIOCARCINOMA

This application is U.S. National Phase of International Application PCT/KR2007/004046, filed Aug. 23, 2007 designating the U.S., and published in English as WO 2008/023947 on Feb. 28, 2008, which claims priority to Korean Patent Application Nos. 10-2006-0079969 and 10-2007-0084868 filed Aug. 23, 2006 and Aug. 23, 2007, respectively.

TECHNICAL FIELD

The present invention relates to a pharmaceutical composition for inhibiting the growth or metastasis of cholangiocarcinoma, comprising a substance inhibiting the activity or expression of L1CAM, which is a protein present on the surface of cholangiocarcinoma cells, and to a treatment method using the composition.

BACKGROUND ART

Cholangiocarcinoma is a cancer of the bile ducts, which drain bile from the liver into the small intestine. Recent evidence has suggested that the liver cancer may arise from a pluripotent hepatic stem cell (Sell and Dunsford Am J. Pathol. 134:1347-1363, 1989). Cholangiocarcinoma entails far lower morbidity worldwide than does liver cancer, with a far higher occurrence in South East Asia than in Europe or North America. Cholangiocarcinoma is not effectively treated by surgical removal because of its high return rate. General chemotherapy and radiotherapy are not useful for the treatment of cholangiocarcinoma (Pederson et al Cancer Res. 4325-4332, 1997) either. In addition, cholangiocarcinoma is difficult to diagnose, and it has been observed that the chronic inflammation, attributed to the infection of bacteria or parasites into the bile ducts, is predisposed to develop into cholangiocarcinoma (Roberts et al., Gastroenterology 112:269-279, 1997).

In spite of the large amount of research results, the pathogenesis of cholangiocarcinoma still remains unknown. Target molecules for the treatment of cholangiocarcinoma are also poorly understood. Only a few cell lines have been established, as a result of some cytogenetic study (Yamaguchi et al., J. Nat'l Cancer Inst 75: 29-35, 1985; Ding et al., Br J Cancer 67: 1007-1010, 1993). However, there has been no report of methods for preparing an antibody specific for cholangiocarcinoma using these cell lines.

Recently, cholangiocarcinoma cell lines Choi-CK and SCK were established from Korean patients suffering from cholangiocarcinoma (Kim et al, Genes, chromosome & Cancer 30:48-56, 2001). If monoclonal antibodies specific to the cell surface are prepared from the mice injected with the cholangiocarcinoma cell line, they can be applied to the treatment of cholangiocarcinoma.

The gene of epidermal growth factor receptor (EGFR), known as a prognostic factor, is a proto-oncogene. EGFR is involved in tumorigenesis and aggressive growth behavior. EGFR is overexpressed in various cancers, including breast cancer, lung cancer, colorectal cancer, kidney cancer, gall bladder carcinoma, head and neck cancer, ovarian cancer, prostate cancer, cancerous cervical tumors, and stomach cancer (Modjtahedi, H. and Dean, C., The receptor for EGF and its ligands: expression, prognostic value and target for therapy in cancer. Int. J. Oncol. 4: 277-296, 1994). In addition, the association of EGFR expression with cancer prognosis differs from one cancer to another (Nicholson, R. I. et al. EGFR and cancer prognosis. Eur. J. Cancer 37, S9-S15, 2001). For example, EGFR can be used as a strong prognosis factor for bladder cancer, cancerous cervical tumors, esophageal cancer, head and neck cancer, and ovarian cancer, but is recognized as a weak prognostic indicator for non-small cell lung carcinoma (NSCLC). However, there is no information known about prognostic factors for cholangiocarcinoma.

When antibodies against EGFR are applied to the treatment of cancers, their inhibitory activity against cancer cell growth was found to vary in efficiency by 15-50% for each cancer type. Also, there is a difference between in vitro and in vivo growth inhibition effects even in the same cancer type (Dassonville, O. et al., EGFR targeting therapies: monoclonal antibodies versus tyrosine kinase inhibitors similarities and differences. Critical Reviews in Oncology/Hematology 62, 53-61, 2007). Currently, antibodies against EGFR are used as therapeutics for colorectal cancer and head and neck cancer, but are not applied to the treatment of all of the above-exemplified cancerous diseases, in which EGFR is overexpressed.

As explained above, expression in cancer cells does not simply guarantee protein to be a prognostic factor for the cancer. Also, whether or not the expression of a protein in cancer cells is associated with cancer prognosis depends on the type of cancer. A strong and poor prognostic factor for cancer can be utilized not only to readily predict the effects of treatment and prognosis of a therapeutic on the cancer, but also to develop a prognostic factor-targeting therapeutic which can be applied selectively and effectively to the cancer of interest. Thus, the discovery of such prognostic factors specific for cancers is very important in the diagnosis and treatment of cancers.

L1 cell adhesion molecule (L1CAM), an integral membrane glycoprotein of 220 kDa, is a member of the immunoglobulin superfamily of cell adhesion molecules (CAMs), which mediate cell-to-cell adhesion on the cell surface. L1CAM, originally identified in neurons (Bateman, et al, EMBO J. 15:6050-6059; 1996), plays a critical role in neural migration, neurite outgrowth and cell migration. The human L1CAM gene was isolated from an embryonic human brain cDNA library using degenerate oligonucleotides derived from L1CAM homologues of mice and rats as probes (Hlavin, M. L. & Lemmon, V. Genomics 11: 416-423, 1991; U.S. Pat. No. 5,872,225, issued on Feb. 16, 1999). L1CAM is expressed primarily in the brain, and its expression is also detected in some normal tissue, and has recently been detected in several types of cancer.

There seems to be an association between L1CAM and cancer. L1CAM has been reported to be expressed in many tumor cell types, including melanoma, neuroblastoma, ovarian carcinoma and colorectal carcinoma (Takeda, et al., J. Neurochem. 66:2338-2349, 1996; Thies et al., Eur. J. Cancer, 38:1708-1716, 2002; Arlt et al., Cancer Res. 66:936-943, 2006; Gavert et al., J. Cell Biol. 168:633-642, 2005). L1CAM has been found not only in the membrane-bound form but also as a cleavage product, which is secreted to the extracellular matrix (Gutwein et al., FASEP J. 17(2):292-4, 2003). Recently, L1CAM has been shown to be a molecule that plays an important role in the growth of tumor cells (Primiano, et al., Cancer Cell. 4(1):41-53 2003) and is arising as a new target for cancer therapy (US2004/0115206 A1, filed on Jun. 17, 2004). Recent studies also showed that L1CAM is expressed at the invasive front of human colon cancer tissue (Gavert, et al., J. Cell Biol. 14; 168(4):633-42. 2005) and anti-L1CAM antibodies function to inhibit the growth and metastasis of ovarian cancer cells (Arlt, et al., Cancer Res. 66:936-943. 2006).

Nowhere is the expression of L1CAM in cholangiocarcinoma cells mentioned in previous reports. Further, there has not yet been any information about whether L1CAM is involved in the growth and metastasis of cholangiocarcinoma. Also, data about whether cholangiocarcinoma patients show higher mortality when L1CAM is expressed at a higher level in the cancer cells, that is, whether L1CAM is a poor prognostic factor for cholangiocarcinoma, have not been published at all. Thus, it was not known prior to the present invention that an antibody against L1CAM has potential as a therapeutic drug by inhibiting the proliferation and metastasis of cholangiocarcinoma, as well.

EP 1,172,654 A1 and U.S. Pat. Publication No. 2004/0259084 disclose a method for the diagnosis and prognosis of an ovarian or endometrial tumors, characterized in that the L1CAM level is determined in a patient sample on the basis that the presence of L1CAM is an indication of the presence of an ovarian or endometrial tumor or a predisposition for such a tumor, and a method of treating ovarian or endometrial tumors in a patient in need of such treatment, comprising administering to the patient a sufficient amount of a L1CAM antibody or a fragment thereof conjugated to a cytotoxic drug. As disclosed in these patents, the L1CAM protein is described only as a marker specific for ovarian or endometrial tumors.

U.S. Pat. Publication No. 2004/0115206 discloses a method and a reagent for inducing cell death in tumor cells using an antibody specifically binding to L1CAM, and pharmaceutical compositions comprising the L1CAM antibody. The method is featured by contacting the tumor cell with an effective amount of an anti-L1CAM antibody for a time and at a concentration sufficient so as to inhibit cell growth or induce cell death in the tumor cell. Mentioning breast cancer, colon cancer and cervical carcinoma cells as examples of L1CAM-expressing tumor cells, this patent publication provides only in-vitro test results, but is not supported by in-vivo data. Nowhere is a relationship between L1CAM and cholangiocarcinoma elucidated therein. Further, this patent publication indicates only that the tumor cell contacts the anti-L1CAM antibody in order to inhibit cell growth and induce cell death, without any suggestion that the anti-L1CAM antibody is able to inhibit the migration, invasion and metastasis of tumor cells.

International Patent Application No. PCT/EP2005/008148 discloses a L1CAM protein overexpressed in ovarian and endometrial carcinoma, a pharmaceutical composition for interfering with the expression of L1CAM, and a method for the prevention and treatment of ovarian and endometrial carcinoma using the composition. The pharmaceutical composition, comprising an anti-L1CAM antibody or a derivative thereof, is described as being able to treat ovarian and endometrial carcinoma by inhibiting the migration and growth of the cancer cells. This patent application also mentions only ovarian and endometrial carcinoma in which L1CAM in a cell-bound form or a soluble form functions to promote the migration of cancer cells.

In brief, none of the literature prior to the present invention discloses that L1CAM is expressed at high levels in cholangiocarcinoma and can thus be used as a poor prognostic factor specific for cholangiocarcinoma, and that a L1CAM inhibitor, such as an antibody to L1CAM, can accordingly be useful in the diagnosis and treatment of cholangiocarcinoma.

DISCLOSURE

Technical Problem

The present inventors conducted intensive and thorough research into the development of antibodies useful in cancer diagnosis and treatment. Mice were immunized with the recently established cholangiocarcinoma cell line (Kim et al., Genes, Chromosomes & Cancer 30:48-56, 2001), thereby obtaining a monoclonal antibody binding specifically to L1CAM on the cholangiocarcinoma cell surface. The obtained monoclonal antibody was designated "A10-A3," and this antibody was found to specifically recognize L1CAM.

Also, L1CAM was found to be expressed on the surface of cholangiocarcinoma cells, but not on the surface of normal cells, such as peripheral lymphocytes, hepatocytes, vascular endothelial cells, etc., as assayed with the A10-A3 antibody and known anti-L1CAM antibodies. L1CAM has been known to be expressed in breast cancer, ovarian cancer, colorectal cancer, skin cancer, etc., but remained unknown about expression on cholangiocarcinoma. Experiments with A10-A3 antibody, conducted by the present inventors, showed that L1CAM was overexpressed in 45.2% of 42 intrahepatic cholangiocarcinoma patients and 39.8% of 103 extrahepatic cholangiocarcinoma patients, particularly in the invasive front, which accounts for the metastasis initiation of cholangiocarcinoma. Also, statistical analysis of the correlation between L1CAM expression rate and survival rate showed that the mortality of cholangiocarcinoma patients with a high L1CAM expression rate was far higher than that of the cholangiocarcinoma patients with a low L1CAM expression rate. Demonstrating that L1CAM is a poor prognostic factor for cholangiocarcinoma, this result indicates that L1CAM can be an important target for the treatment of cholangiocarcinoma.

Although expressed at a high level in cholangiocarcinoma, in contrast, EGFR, which is used as a target of therapeutic agents for current clinical use in the treatment of colon cancer (e.g., cetuximab, a chimeric antibody to EGFR), was proven not to be a poor prognostic factor for cholangiocarcinoma because no statistical significance was found in the analysis of a correlation between EGFR expression rates and survival rates. Thus, EFGR is recognized not to be a poor prognostic factor for cholangiocarcinoma. Thus, not all of the molecules overexpressed in cancer can be used as important targets for the treatment thereof.

When L1CAM expression was suppressed by introducing siRNA against L1CAM into L1CAM-expressing cholangiocarcinoma cell lines (Choi-CK, SCK), the growth, migration and invasion thereof was found to be suppressed. These results indicate that L1CAM plays an important role in the growth and metastasis of cholangiocarcinoma.

Antibodies to L1CAM were found to have inhibitory activity against the growth, migration or invasion of cholangiocarcinoma cells, as assayed by treating cholangiocarcinoma cell lines (Choi-CK, SCK) with A10-A3 antibody or a known anti-L1CAM antibody (UJ127). In addition, the injection of A10-A3 antibody inhibited the growth of cholangiocarcinoma cells in nude mice which were transplanted with a cholangiocarcinoma cell line. Further, the monoclonal antibody 4-63, produced by a hybridoma (KCTC 10966BP) obtained from mice immunized with human embryonic stem cells, recognized L1CAM on the cancer cell surface, and inhibited the growth of cholangiocarcinoma. Leading to the present invention, thus, thorough and intensive research, conducted by the present inventors, has led to the conclusion that anti-L1CAM antibodies are useful in the diagnosis and treatment of cholangiocarcinoma.

Technical Solution

It is therefore an object of the present invention to provide a pharmaceutical composition for inhibiting the growth and metastasis of cholangiocarcinoma, comprising a substance inhibiting the activity of L1CAM or suppressing the expression of L1CAM.

It is another object of the present invention to provide a method of treating cholangiocarcinoma based on the use of the pharmaceutical composition.

It is a further object of the present invention to provide an anti-L1CAM antibody to inhibit the activity of L1CAM.

It is yet another object of the present invention to provide an oligonucleotide to inhibit the expression of L1CAM.

It is still another object of the present invention to provide a method of inhibiting the proliferation or metastasis of cholangiocarcinoma cells based on the use of the pharmaceutical composition.

DESCRIPTION OF DRAWINGS

FIG. 1 shows the results of fluorescent cell staining and flow cytometry for the binding capacity of mouse monoclonal antibodies, A10-A3 (A) and 4-63 (B), and known antibodies 5G3 (C) and UJ127 (D) to the cell surface of various carcinoma cell lines including cholangiocarcinoma, and normal cells.

FIG. 2 shows the results of immunoprecipitation and Western blotting, indicating that A10-A3 specifically binds to L1CAM. A: The cell surface of Choi-CK cholangiocarcinoma was biotinylated, and immunoprecipitation was carried out with the A10-A3 antibody or a known anti-L1CAM monoclonal antibody (UJ127). Precipitated proteins were subjected to 10% SDS-PAGE and Western blotting with Streptavidin-HRP. L1CAM was detected by Western blotting. B: Proteins were immunoprecipitated with A10-A3 antibody, separated on 10% SDS-PAGE and subjected to Western blotting using the known anti-L1CAM antibody (UJ127). L1CAM was detected by Western blotting. "Preclearing," as a negative control, indicates immunoprecipitation (IP) in the absence of the antibody, "IP with A10-A3" indicates IP using A10-A3 antibody, "IP with anti-L1CAM" indicates IP using a known anti-L1CAM monoclonal antibody, and "A10-A3 only" indicates SDS-PAGE of the antibody only. C: Soluble L1-expressing HEK293T cells were subjected to Western blotting using known antibodies, UJ127 and 5G3, and A10-A3 and 4-63 antibodies. "−" indicates a culture supernatant of cells not carrying L1 expression vector, and "+" indicates a culture supernatant of cells containing a soluble L1 expression vector.

FIG. 3 shows the results of Q-TOF analysis. Proteins from Choi-CK cells were immunoprecipitated with an A10-A3 antibody, separated on SDS-PAGE, and trypsin-digested. The obtained peptides were analyzed using Q-TOF, which revealed that the immunoprecipitated protein is L1CAM. The lower amino acid sequence represents the full-length L1CAM (SEQ ID NO: 11), and upper amino acid sequences show the sequences of the analyzed peptides (SEQ ID NOs: 4-10), corresponding to the underlined parts of the full-length L1CAM sequence.

FIG. 4 shows the results of the immunohistochemical staining of carcinoma tissues from cancer patients using A10-A3 (A and C) and 4-63 (B) antibodies. The antibodies were found to bind to human cholangiocarcinoma tissues but not to bind to normal hepatic tissues.

FIG. 5 provides tables in which correlations between L1CAM expression in intrahepatic cholangiocarcinoma (A) and extrahepatic cholangiocarcinoma (B) and clinicopathological properties are summarized.

FIG. 6 provides graphs showing correlations between L1CAM expression rate and survival rates of extrahepatic cholangiocarcinoma patients (60 cases) expressed as both OS (overall survival) and DFS (disease free survival).

FIG. 7 shows L1CAM expression levels in cholangiocarcinoma cells transfected with siRNA against L1CAM and non-specific siRNA (A) and the degrees of proliferation, invasion and migration of the transfected cells (B).

FIG. 8 shows the inhibitory effects of anti-L1CAM antibodies A10-A3 (A), 4-63 (B) and UJ127 and 5G3 (C) on the growth of the cholangiocarcinoma cell line Choi-CK and SCK. The ovarian cancer cell line SK-OV3 and the renal cancer cell line ACHN, to which the A10-A3 antibody did not bind, were used as a positive cell control and a negative cell control, respectively. For a negative antibody control, treatment with no antibody (control), a heat-inactivated antibody (boiled A10-A3b or 4-63b) or normal mouse IgG was conducted. The degree of cell growth was expressed as a percentage relative to a control not containing any antibody after the cells were incubated for 72 hours with 10 µg/ml of antibody.

FIG. 9 shows the inhibitory effects of the anti-L1CAM antibodies A10-A3, 4-63 and 5G3 on the invasion and migration of cholangiocarcinoma cells (Choi-CK, SCK). The renal cancer cell line ACHN, to which the A10-A3 antibody did not bind, was used as a negative cell control while, for a negative antibody control, treatment with no antibody (control), a heat-inactivated antibody (boiled A10-A3b or 4-63b) or normal mouse IgG was conducted. The degree of cell growth was expressed as a percentage relative to a control not containing any antibody after the cells were incubated for 72 hours with 10 µg/ml of antibody.

FIG. 10 shows that the A10-A3 antibody inhibits signal transduction involved in the growth, migration and survival of cancer cells. The cholangiocarcinoma cell line Choi-CK or SCK was treated with A10-A3 antibody or mouse IgG, or was not treated with any antibody, and was then collected. Cell lysates were subjected to Western blotting using antibodies against PCNA (A), phospho-MAPK (A), phospho-AKT (B) and phospho-FAK (C). An anti-β-actin antibody was used to detect β-actin as a loading control.

FIG. 11 shows the inhibitory effect of A10-A3 antibody on cancer growth in human cholangiocarcinoma xenograft mouse models. Panel A shows changes in tumor volume over time in 5 mice administered with the antibody (A10-A3 group) and 5 mice not administered with an antibody (control). Panel 11B shows weights of tumors three weeks after the transplantation of cancer cells. Panel C shows the cancer tissues in photographs. Panel D is a graph in which the body weights of the mice were monitored for a period of time.

BEST MODE

In one aspect, the present invention is directed to a pharmaceutical composition for inhibiting the growth or metastasis of cholangiocarcinoma, comprising a substance inhibiting the activity of L1CAM or suppressing the expression of L1CAM.

In one embodiment thereof, the present invention provides a pharmaceutical composition comprising a substance inhibiting the activity of L1CAM. Preferably, the activity-inhibiting substance is an antibody that specifically recognizes a cholangiocarcinoma cell surface antigen or a secreted surface antigen (L1CAM). The antibody includes all monoclonal antibodies and chimeric antibodies, humanized antibodies and human antibodies thereof. Novel antibodies, as well as antibodies known in the art, fall within the scope of the present invention. Preferable is a novel anti-L1CAM monoclonal antibody A10-A3 or 4-63, a known anti-L1CAM monoclonal antibody UJ127, or a chimeric, humanized or human antibody thereof. The A10-A3 and 63 antibodies are secreted by hybridomas having KCTC accession numbers KCTC 10909BP and KCTC 10966BP, respectively.

As long as they have the binding specificity for L1CAM, the antibodies include complete forms having two full-length light chains and two full-length heavy chains, or may be in the form of functional fragments of antibody molecules. As used herein, the term "functional fragments of antibody molecules" is intended to refer to fragments retaining at least an antigen-binding function, which are exemplified by Fab, F(ab), F(ab')$_2$ and Fv.

In another embodiment of this aspect, according to the present invention, the pharmaceutical composition may include a substance suppressing the expression of L1CAM. When its expression level in L1CAM-expressing tumor cells is suppressed by an L1CAM expression inhibitor, the growth and metastasis of tumor cells decrease, which can be therefore applied to the treatment of such cancers. Preferably, the L1CAM expression inhibitor is selected from the group consisting of siRNAs, shRNAs and antisense oligonucleotides, and is preferably an siRNA containing a sequence of 5'-TGGTACAGTCTGGGdtdt-3' (SEQ ID NO: 1) or 5'-CAGCAACTTTGCTCAGAGGdtdt-3' (SEQ ID NO: 2).

As used herein, the term "siRNA" is intended to refer to a small nucleic acid molecule of about 20 nucleotides, which mediates RNA interference or gene silencing. The term "shRNA" refers to a short hairpin RNA in which sense and antisense sequences of a siRNA target sequence are separated by a loop structure of 5 to 9 bases. Recently, the phenomenon of RNA interference (RNAi) has been studied for application to a method for controlling protein expression at the gene level. Typically, siRNA has been shown to inhibit protein expression by binding specifically to mRNA, having a sequence complementary to a target gene.

siRNA, which is contained in the composition according to the present invention, can be prepared by direct chemical synthesis (Sui G et. al, (2002) *Proc Natl Acad Sci USA* 99:5515-5520) or in vitro transcription (Brummelkamp T R et al., (2002) *Science* 296:550-553), but the present invention is not limited to these methods. Also, shRNAs that are designed to overcome the drawbacks of siRNAs, including expensive siRNA biosynthesis and low transfection efficiency, leading to the short-term persistence of the RNA interference effect, can be expressed from an RNA polymerase III-based promoter contained in an adenoviral, lentiviral or plasmid expression vector system, which has been introduced into cells. The shRNA molecules are processed into functional siRNA molecules using an siRNA processing enzyme (Dicer or RNase III) within the cells, and then induce the silencing of a target gene.

As used herein, the term "antisense" is intended to refer to an oligomer having a sequence of nucleotide bases and a subunit-to-subunit backbone that allows the antisense oligomer to hybridize with a target sequence in RNA by Watson-Crick base pairing to form an RNA:oligomer heteroduplex within the target sequence, typically with mRNA. The oligomer may have exact sequence complementarity to the target sequence, or near complementarity thereto. These antisense oligomers may block or inhibit the translation of the mRNA, and/or modify the processing of mRNA to produce a splice variant of the mRNA. Thus, the antisense oligomer of the present invention is an antisense oligomer complementary to the mRNA of the L1CAM gene.

Preferably, the composition according to the present invention may include a known therapeutic agent, which is directly or indirectly conjugated to the antibody or is present in a non-conjugated form. The therapeutic agent capable of binding to the antibody includes, but is not limited to, radionuclides, drugs, lymphokines, toxins and bispecific antibodies. As long as it can exert therapeutic effects on cancer when conjugated to an antibody or administered in combination with a siRNA, a shRNA or an antisense oligonucleotide, any known therapeutic agent can be used in the present invention.

Examples of the radionuclides include, but are not limited to, $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

The drugs and toxins useful in the present invention include etoposide, teniposide, adriamycin, daunomycin, caminomycin, aminopterin, dactinomycin, mitomycin, cis-platinum and cis-platinum analogues, bleomycins, esperamicins, 5-fluorouracil, melphalan, and nitrogen mustard, but are not limited thereto.

Preferably, the composition according to the present invention may include an acceptable carrier appropriate to the administration mode thereof.

Formulations suitable for administration modes are known in the art. Also, the pharmaceutical composition of the present invention may be administered in a pharmaceutically effective amount for cancer treatment. The typical dosage may be optimized using a standard clinical technique.

In accordance with another aspect thereof, the present invention is directed to a method of treating cholangiocarcinoma based on the use of the pharmaceutical composition.

In greater detail, the method comprises administering a pharmaceutically effective amount of the pharmaceutical composition to the body. The pharmaceutical composition may be administered parenterally, subcutaneously, intrapulmonarily or intranasally. For local immunosuppressive therapy, the composition may, if desired, be administered using a suitable method, including intralesional administration. Parenteral injections include intramuscular, intravenous, intraarterial, intraperitoneal and subcutaneous routes. Preferred administration modes include intravenous, subcutaneous, intradermal, intramuscular and drip injections.

Cholangiocarcinoma may be treated by administering the pharmaceutical composition of the present invention to the body, wherein an L1CAM-specific antibody, contained in the composition, binds to the cancer cell surface antigen L1CAM, thereby inhibiting the proliferation or metastasis of cholangiocarcinoma cells.

Also, cholangiocarcinoma may be treated by administering the pharmaceutical composition of the present invention to the body to allow the antibody to bind to secreted L1CAM, which induces the blockage of the growth and metastasis of cancer cells. Alternatively, the antibody, when injected, binds to the cancer cell surface antigen L1CAM, so that immune cells recognize this association, leading to the phagocytosis, apoptosis or killing of the cancer cells.

Cholangiocarcinoma treatment may also be achieved by inhibiting the expression of L1CAM using the L1CAM expression inhibitor contained in the pharmaceutical composition of the present invention. In this case, the stimulatory action of L1CAM on the growth and metastasis of cholangiocarcinoma cells decreases.

In accordance with a further aspect thereof, the present invention is directed to an antibody against L1CAM for inhibiting the activity of L1CAM or an oligonucleotide against L1CAM for inhibiting the expression of L1CAM.

In one embodiment of this aspect, as described for the composition according to the present invention, the antibody, as long as it binds specifically to L1CAM, includes complete forms having two full-length light chains and two full-length heavy chains, as well as functional fragments of antibody molecules. The functional fragments of antibody molecules are fragments that retain at least an antigen-binding function, and include Fab, F(ab), F(ab')$_2$ and Fv.

Preferably, the antibody recognizes the cholangiocarcinoma cell surface antigen or secreted surface antigen (L1CAM). The antibody is characterized in that it binds to the cholangiocarcinoma cell surface protein L1CAM to inhibit or neutralize the action of L1CAM, and that, through binding to cancer cells, it inhibits the growth and metastasis of the cells, phagocytosizes the cells, induces apoptosis within the cells, or kills the cells.

As described in Application US20040115206, anti-L1CAM antibodies do not always inhibit the action of L1CAM. The present antibody is characterized in that it does not stimulate the action of L1CAM but inhibits the activity of L1CAM.

More preferably, the antibody is a novel monoclonal antibody, A10-A3 or 4-63.

In another embodiment, the present oligonucleotide against L1CAM, functioning to suppress the expression of L1CAM, is selected from among siRNAs, shRNAs and antisense oligonucleotides against L1CAM, which are specified for the present composition.

In a further embodiment, cholangiocarcinoma cells were cultured on a large scale and injected into the foot pads of mice. Lymphocytes were extracted from the lymph nodes of mice and fused with myeloma tumor cells to yield mouse hybridomas producing antibodies binding to cholangiocarcinoma cells.

In detail, cholangiocarcinoma cell lines SCK and Choi-CK were injected into the foot pads of mice, and lymphocytes were extracted from the lymph nodes of mice. The isolated lymphocytes were fused with F0 myeloma cells, and clones expressing antibodies were selected. Among the selected clones, supernatants of hybridomas that secreted monoclonal antibodies relatively stably were tested for binding capacity to cholangiocarcinoma cells. A monoclonal antibody-secreting hybridoma thus established was designated "hybridoma A10-A3". The hybridoma was deposited with an international depositary authority, KCTC (Korean Collection for Type Cultures; Korean Research Institute of Bioscience and Biotechnology (KRIBB), Korea) on Feb. 20, 2006, and assigned accession number KCTC10909BP.

Separately, another antibody recognizing L1CAM, 4-63, was obtained using human embryonic stem cells, and was found to bind to cholangiocarcinoma and lung carcinoma cells. A hybridoma secreting the 4-63 antibody was deposited at KCTC and assigned accession number KCTC10966BP. In detail, the monoclonal antibodies were found to bind to carcinoma cell lines, such as cholangiocarcinoma (see, FIG. 1), but not to bind to normal cells, including hepatocytes, HUVEC (human umbilical vein endothelial cells) or peripheral blood lymphocytes (see, FIG. 1). The antibodies inhibited the growth, migration or invasion of cholangiocarcinoma. Also, a known anti-L1CAM antibody 5G3 was observed to bind to cholangiocarcinoma cells, but to inhibit cancer growth only at a low efficiency (see, FIG. 8), while another known anti-L1CAM antibody UJ127 was found to bind to cholangiocarcinoma cells and thus to inhibit the growth of the cells. These results indicate that anti-L1CAM antibodies do not always inhibit the action of L1CAM.

In another embodiment of the present invention, the expression level of L1CAM was found to be lower in Choi-CK and SCK cell lines transfected respectively with siRNA sequences of 5-TGGTACAGTCTGGGdtdt-3 (SEQ ID NO: 1) and 5-CAGCAACTTTGCTCAGAGGdtdt-3 (SEQ ID NO: 2) than in the same cell lines transfected with non-specific oligonucleotides. Also, it was observed that a cancer cell group with siRNA knock-down of L1CAM was decreased in proliferation, invasion and migration compared to a cancer cell group that expressed L1CAM normally.

As proven in Examples of the present invention (refer to Examples 5, 6 and 7), the present inventors discovered first that L1CAM is expressed in cholangiocarcinoma cells to the extent of overexpression in about 40% of cholangiocarcinoma patients. It was also first revealed by the present inventors that L1CAM is a poor prognostic factor which plays an important role in the tumor progression of cholangiocarcinoma cells to thus increase the risk of death, and that EGFR, previously known to be a poor prognostic factor for cancer, is not a poor indicator for cholangiocarcinoma. Thus, inhibitors against the activity or expression of L1CAM in accordance with the present invention can be specifically applied to the diagnosis and treatment of LiCAM-expressed cancers, especially, cholangiocarcinoma.

Besides, immunohistochemical staining assays showed that LiCAM is expressed at a level below 10% on non-small cell lung carcinoma (NSCLC) cells. When the L1CAM-expressing NSCLC cell lines A549 and NCI-H522 were treated with the A10-A3 antibody, their growth was inhibited in amounts of 14% and 24%, respectively, which fall far short of 40%, the approximate inhibition rate of A10-A3 on the growth of cholangiocarcinoma, demonstrating that the composition of the present invention is therapeutically effective especially for cholangiocarcinoma. This comparison is further described in a Korean Patent Application (entitled, A Pharmaceutical Composition for Treating Cholangiocarcinoma, A Method for Inhibiting Growth or Invasion of Cholangiocarcinoma and a Method for Treating Cholangiocarcinoma), filed on the same date as the present application, the entire contents of which are incorporated herein by reference.

A better understanding of the present invention may be obtained through the following examples, which are set forth to illustrate, but are not to be construed as the limit of the present invention.

MODE FOR INVENTION

Example 1

Culture of Cancer Cells

Carcinoma cell lines were cultured using the following media, containing 10% fetal bovine serum (FBS; Gibco) in an incubator at 37° C. under 5% $CO_2$. SH-J1 (hepatocellular carcinoma), SCK (cholangiocarcinoma), Choi-CK (cholangiocarcinoma) and ACHN (Renal cell adenocarcinoma) cells were cultured using MEM medium (Gibco), and SK-OV3 (ovary adenocarcinoma) cells were cultured using McCoy 5A Medium (Gibco). A549 (non small cell lung carcinoma) cells were cultured in Ham's F12K medium, and NCI-H522 (non small cell lung carcinoma), DMS114 (small cell lung carcinoma), DMS53 (small cell lung carcinoma) and NCI-H69 (small cell lung carcinoma) cells were cultured in RPMI1640 medium. SH-J1, SCK and Choi-CK cell lines were gifts from Dr. Daegon Kim (Medical School, Chonbuk National University), and other carcinoma cell lines were purchased from ATCC. Normal hepatocytes and HUVEC (human umbilical vein endothelial cells), which all were purchased from Cambrax, were cultured using 10% FBS (Gibco)-containing EGM-2 medium (Hyclone) in an incubator at 37° C. under 5% $CO_2$. Peripheral blood lymphocytes (PBL) were isolated from human blood by Ficoll-gradient centrifugation.

Example 2

Preparation of A10-A3 Monoclonal Antibody Binding to Cancer Cells Choi-CK and SCK The cultured Choi-CK and SCK carcinoma cells were detached using cell dissociation buffer (Invitrogen), and $5\times10^5$ cells were suspended in 30 μl of PBS. Balb/c mice were injected with Choi-CK cells in the right foot pad, and with SCK cells in the left foot pad 3 days later. Mice were then boosted six times at 3-4 day intervals, and were finally immunized one day before cell fusion. The culture of F0 myeloma cells (ATCC, USA), to be fused with lymph node cells, was commenced in 10% FBS-containing DMEM (Gibco) two weeks before cell fusion. Popliteal lymph nodes were removed from the mice immunized with Choi-CK and SCK cells, washed well with DMEM medium (Gibco) and finely teased. The cell suspension was transferred into a 15-ml tube. F0 myeloma cells were harvested by centrifugation, suspended in 10 ml of DMEM medium, and counted along with the lymph node cells. Then, $10^6$ F0 myeloma cells and $10^7$ lymph node cells were mixed in a 50-ml tube and centrifuged at 200×g for 5 min. After the supernatant was discarded, the tube was incubated for 2 min in a beaker containing water at 37° C. After the tube was tapped to loosen the cell pellet, 1 ml of PEG (Gibco) was slowly added over one minute to the tube while the tube was gently shaken in a water bath at 37° C. After the cells were centrifuged at 100×g for 2 min, 5 ml of DMEM medium was slowly added over 3 min to the tube, and 5 ml of DMEM medium was further added slowly over 2 min. The cells were then harvested by centrifugation at 200×g. In order to increase cell fusion efficiency and cell viability, the basal medium (DMEM+20% FBS) was supplemented in advance with 10% Hybridoma Cloning Factor (BioVeris, USA). The recovered cells were carefully suspended in 30 ml of the normal medium (DMEM+20% FBS) supplemented with Hybridoma Cloning Factor. After the cell suspension was incubated in a $CO_2$ incubator at 37° C. for 30 min, $10^5$ cells (70 μl) were aliquotted into a 96-well plate and incubated in a $CO_2$ incubator at 37° C. The next day, 70 μl of HAT medium was added to each well, and the plate was observed for whether colonies were formed in HAT medium at 3-day intervals for a period of over 2 weeks. The culture supernatants of hybridoma colonies, obtained by fusing lymphocytes, isolated from lymph nodes from mice immunized with Choi-CK cells and from lymph nodes from mice immunized with SCK cells, with myeloma cells, were used in the following tests.

Clones expressing antibodies were selected using sandwich ELISA (Enzyme Linked Immunosorbent Assay). 100 μl of the hybridoma culture was added to a plate coated with 2 μg/ml of anti-mouse IgG or IgM antibody and allowed to react at 37° C. for 1 hr. The plate was then incubated for 1 hr in a 1:5,000 dilution of horseradish peroxidase (HRP; Sigma)-conjugated anti-mouse IgG or IgM antibody. After the plate was washed with 0.08% Tween 20-containing phosphate buffer, a substrate solution containing OPD (Sigma) and $H_2O_2$ was added to each well, and absorbance was measured at 492 nm using a spectrophotometer in order to select clones producing antibodies.

Among the selected clones, the culture supernatants of hybridomas that secreted a monoclonal antibody relatively stably were tested for binding capacity to SCK and Choi-CK cells. In detail, the cultured Choi-CK cells were treated with cell dissociation buffer (Gibco) for 20 min at 37° C. to be dissociated into single cells, and were passed through a 40-μm strainer. $5\times10^5$ cells were used in flow cytometry. The SCK and Choi-CK cells, dissociated into single cells, were suspended in PBA (1% BSA in PBS), and antibody supernatants were allowed to react at 4° C. for 30 min. After the cells were centrifuged at 1200 rpm for 5 min, 100 μl of the supernatant was discarded, and the cells were allowed to react with a 1:200 dilution of anti-mouse Ig-FITC (BD) at 4° C. for 30 min. After the cells were washed with PBA twice, propidium iodide (PI)-negative cells were selected and evaluated for binding capacity to SCK and Choi-CK cells using a FACS caliber.

Various hybridomas secreting antibodies binding to SCK and Choi-CK cells were selected, stabilized through continuous subculture, and then subcloned. A hybridoma secreting an antibody, A10-A3, stably maintaining the specificity to SCK and Choi-CK cells through subcloning, was selected.

The hybridoma secreting the A10-A3 antibody was designated "hybridoma A10-A3". The hybridoma was deposited at KCTC (Korean Collection for Type Cultures; Korean Research Institute of Bioscience and Biotechnology (KRIBB), 52, Oun-dong, Yusong-ku, Taejon, Korea)) on Feb. 20, 2006 and assigned accession number KCTC10909BP.

Example 3

Evaluation of Cell Surface Expression of L1CAM in Lung Carcinoma Cell Lines

The hybridoma A10-A3 cell line was cultured in a serum-free medium (PFHM, Invitrogen), and the secreted A10-A3 antibody was purified using a protein G-Sepharose column (Pharmacia, Sweden) (Fike et al., Focus 12: 79, 1990). The purified A10-A3 antibody was evaluated for binding capacity for cholangiocarcinoma cells using fluorescent staining according to the same method as in Example 3 (FIG. 1). In FIG. 1, empty peaks outlined with solid lines represent samples treated with the monoclonal antibodies A10-A3 and 4-63 and the known anti-L1CAM antibodies 5G3 (Pharmingen, San Diego, USA) and UJ127 (Chemicon), while the filled peak is background fluorescence in the presence of the secondary antibody alone. The binding capacity of A10-A3, 4-63, 5G3 and UJ127 antibodies for various carcinoma cells was analyzed using FACS caliber. FACS analysis revealed that the monoclonal antibodies bind to NCI-H522, A549, DMS114, DMS53 and NCI-H69 lung carcinoma cells (panels A, B, C and D, FIG. 1), while they do not bind to ACHN carcinoma cells, normal cells, hepatocytes, HUVEC or peripheral blood lymphocytes (PBL).

Example 4

Isolation and Identification of Antigen Recognized by the Monoclonal Antibody A10-A3

Example 4-1

Antigen Isolation

A cell surface protein recognized by the monoclonal antibody A10-A3 was isolated as follows. First, Choi-CK cells were washed with PBS and biotinylated with EZ-Link Sulfo-NHS-LC-Biotin (Pierce, Rockford, Ill.). The cells were incubated in lysis buffer (25 mM Tris-HCl, pH 7.5, 250 mM NaCl, 5 mM EDTA, 1% Nonidet P-40, 2 µl/ml aprotinin, 100 µg/ml phenylmethylsulfonyl fluoride, 5 µg/ml leupeptin) at 4° C. for 20 min. After the cells were centrifuged to remove cell debris, the supernatant was recovered, and protein concentrations were determined using a bicinchoninic acid (BCA) protein assay kit (Pierce).

The cell lysate was allowed to react with 20 µl of protein G plus-sepharose (Santa Cruz Biotechnology, Santa Cruz) at 4° C. for 2 hrs, and was centrifuged to remove proteins non-specifically binding to protein G plus-sepharose. The supernatant was recovered and allowed to react with about 1 µg of antibody at 4° C. for 12 hrs. Twenty µl of protein G plus-sepharose was added to the reaction mixture, followed by incubation at 4° C. for 2 hrs. The reaction mixture was centrifuged, and the precipitate was recovered. The recovered precipitate was washed with cell lysis buffer more than ten times, and the remaining proteins were separated using 10% SDS-PAGE.

The proteins were transferred onto a nitrocellulose membrane and subjected to Western blotting. The nitrocellulose membrane was blocked with 5% skim milk-containing PBST (PBS+0.1% Tween 20) for 1 hr, and washed with PBST more than twice. The blot was then incubated for 1 hr with Streptavidin-horseradish peroxidase (HRP) conjugate (1:1,500; Amersham Biosciences). After the blot was washed with PBST five times, biotinylated proteins were developed with an ECL reagent (Amersham Biosciences).

The A10-A3 antibody was found to bind to a protein of about 200 kDa (panel A, FIG. 2). In order to collect a protein immunoprecipitated by the A10-A3 antibody, cell lysates from $1 \times 10^8$ Choi-CK cells were subjected to immunoprecipitation according to the same method as described above, and electrophoresed on a SDS-PAGE gel. The gel was stained with Coomassie G250 (Biorad).

Example 4-2

Antigen Identification Using Mass Spectrometry

The SDS gel containing a protein immunoprecipitated by the A10-A3 antibody was stained with Coomassie G250 (BIO-RAD). A protein band was excised from the gel, washed with 30% methanol for 5 min, and finely cut. The gel pieces were dehydrated in 100% acetonitrile for 10 min, and completely dried in a vacuum centrifuge for 30 min. The dried gel pieces were incubated with 300 ng of trypsin (Promega) in 50 mM ammonium bicarbonate for 16 hrs at 37° C. The digested peptides were extracted with 100 µl of 50 mM ammonium bicarbonate three times, and dried in the vacuum centrifuge. The peptide mixture was analyzed using electrospray quadrupole time-of-flight tandem mass spectrometry (ESI Q-TOF MS/MS) (Q-TOF micro, MicroMass). The protein recognized by the A10-A3 antibody was identified as the L1 Cell Adhesion molecule (L1CAM) (FIG. 3). In FIG. 3, the underlined region represents the amino acid sequence actually identified by Q-TOF. Thus, as described in Example 3-1, a biotin-labeled Choi-CK cell lysate was immunoprecipitated with the anti-L1CAM monoclonal antibody JU127.11, purchased from Chemicon (USA), and the blot was developed with ECL. As shown in panel A of FIG. 2, the A10-A3 antibody and the anti-L1CAM antibody were found to immunoprecipitate a protein at the same molecular size of about 200 kDa.

Example 4-3

Identification of L1CAM Antigen Using Western Blotting

In order to confirm that the A10-A3 antibody recognizes L1CAM, immunoprecipitation was carried out in a Choi-CK cell lysate using the A10-A3 antibody.

The cell lysate was allowed to react with 20 µl of protein G plus-sepharose (Santa Cruz Biotechnology, Santa Cruz) at 4° C. for 2 hrs, and centrifuged to remove proteins non-specifically binding to protein G plus-sepharose. The supernatant was recovered and allowed to react with about 1 µg of antibody at 4° C. for 12 hrs. Twenty µl of protein G plus-sepharose was added to the reaction mixture, followed by incubation at 4° C. for 2 hrs. The reaction mixture was centrifuged, and the precipitate was recovered (preclearing of FIG. 2). The recovered precipitate was washed with cell lysis buffer more than ten times, and remaining proteins were separated on 10% SDS-PAGE without mercaptoethanol.

The proteins were transferred onto a nitrocellulose membrane and subjected to Western blotting. The nitrocellulose membrane was blocked with 5% skim milk-containing PBST (PBS+0.1% Tween 20) for 1 hr, and washed with PBST more than twice. The blot was then incubated for 1 hr in the known anti-L1CAM antibody UJ127 (Chemicon) as the primary antibody. After being washed with PBST five times, the blot was incubated for 1 hr with anti-mouse IgG-HRP conjugate (1:1,500; Sigma). After the blot was washed with PBST five times, biotinylated proteins were developed with an ECL reagent (Amersham biosciences). The anti-L1CAM antibody was found to bind to a protein of about 200 kDa, which was immunoprecipitated with the A10-A3 antibody (panel B, FIG. 2). This result confirmed that the A10-A3 antibody recognizes L1CAM.

Example 4-4

Expression of Soluble L1CAM

In order to construct an expression vector for expressing soluble L1CAM, total RNA was isolated from Choi-CK carcinoma cells using an RNA extraction kit (Roche co.). Using an RT-PCR kit (Roche Co.), PCR was carried out using the isolated total RNA as a template, two terminal primers Ig-dom-F (5'-GAG GAG GAA TTC CGG CGC CGG GAA AGA TGG TCG TGG CG-3', 38 mer) (SEQ ID NO: 12) and L1-Fn-Stop-R (5'-CTC TAG AGT TCT CGA GTC AGA GCC TCA CGC GGC C-3', 34 mer) (SEQ ID NO: 13), and pfu polymerase (Solgent Co.). PCR conditions included pre-incubation at 95° C. for 5 min, 25 cycles of 30 sec at 95° C., 30 sec at 58° C. and 2 min at 72° C., and finally elongation for 10 min at 72° C.

The amplified soluble L1 DNA fragment was digested with EcoR I and Xho I and electrophoresed on a 1% agarose gel. The L1 DNA fragment was excised from the gel and purified with a gel purification kit (Intron co.). The digested L1 DNA fragment was ligated with a pJK-dhfr2 expression vector (Aprogen), digested with EcoR I and Xho I using T4 DNA ligase (Roche co.) at 16° C. for 30 min, and transformed into *E. coli* DH5 α by heat shock. Plasmid DNA was isolated from the transformed cells, and the DNA sequence thereof was determined. DNA sequencing revealed that cDNA of soluble L1CAM was successfully cloned. The expression vector thus obtained was designated "pJK-dhfr2-L1-monomer".

pJK-dhfr2-L1-monomer DNA was transfected into HEK293T cells (ATCC CRL11268, hereinafter referred to as 293T) in order to express soluble L1CAM in the monomer form.

Ten μg of the expression vector DNA and Lipofectamine 2000 (Invitrogen co.) were added individually to 500 μl of Opti-MEM medium (Gibco BRL), and were allowed to stand at room temperature for 5 min. Then, the vector DNA was mixed with lipofectamine, and the mixture was allowed to react at room temperature for 15 min. During the formation of DNA-lipofectamine complexes, 293T cells were carefully washed with PBS (pH 7.4), and Opti-MEM medium was carefully added to the cells and was then removed. The DNA-lipofectamine complexes were mixed with 4 ml of Opti-MEM medium, and carefully dropped over the cells. The cells were incubated in an incubator at 37° C. After 6 hrs, the cells were re-fed with 5 ml of Opti-MEM medium, and further cultured for 3 days.

Example 4-5

Evaluation of Binding Specificity of Antibodies to Soluble L1CAM

A culture fluid of 293T cells expressing soluble L1CAM and another culture fluid of 293T cells not expressing soluble L1CAM were subjected to 10% SDS-PAGE and then to Western blotting. The nitrocellulose membrane was blocked with 5% skim milk-containing TBST (TBS+0.05% Tween 20) at 4° C. for 12 hrs, and washed with TBST more than twice. The blot was then incubated for 1 hr with primary antibodies, the known anti-L1CAM antibodies UJ127 (Chemicon) and 5G3 (Pharmingen), and the A10-A3 and 4-63 antibodies, each antibody diluted 1:10,000 in 5% skim milk-containing TBST. After being washed with TBST five times, the blot was incubated for 1 hr with anti-mouse IgG-HRP conjugate (1:5000; Sigma). The blot was washed with PBST five times and developed with an ECL reagent (Amersham biosciences). Each antibody was found to bind to soluble L1CAM of about 200 kDa (panel C, FIG. 2). Also, ELISA for the L1-expressed cell culture using the above antibodies revealed that each antibody has binding specificity for the expressed soluble L1CAM.

Example 5

Immunohistochemical Staining of Cholangiocarcinoma Tissue

Sections 3 μm thick were prepared from tumors for the immunohistochemical staining of cholangiocarcinoma tissues. The sections were placed on a slide coated with poly-L-lysine and dried at 60° C. for 3 hrs. The sections were then deparaffinized in xylene at room temperature for 5 min three times, and hydrated in 100%, 90%, 80% and then 70% alcohol for 1 min each. The slide was dipped in a target retrieval solution (DAKO, Carpinteria, Calif.) to recover antigenicity, and was washed with TBST (Tris-buffered saline-Tween 20), which was pre-boiled for 4 min using a pressure cooker. A biotin-free Tyramide Signal Amplification System, CSA II (DAKO, Carpinteria, Calif.) was used for highly sensitive detection for immunohistochemical staining. The slide was incubated in 3% hydrogen peroxide for 5 min to block the non-specific binding of antibodies. After being washed with TBST twice for 5 min each time, the sections were incubated in sufficient serum-free protein block for 5 min to block the non-specific binding of proteins. The tissue sections were incubated with primary antibodies (A10-A3 and 4-63, 1:50 dilution) for 15 min, and then with anti-mouse immunoglobulin-HRP for 15 min. The sections were then incubated with an amplification reagent and anti-fluorescein-HRP for 15 min each. Finally, the sections were stained with DAB for 5 min and counter-stained with Meyer's hematoxylin, followed by TBST washing for 5 min twice. A negative control was stained according to the same procedure as described above, except that normal sheep serum not containing the primary antibody, or normal mouse IgG1 serum, was used in place of the primary antibody. Neither of the A10-A3 or 4-63 antibodies were found to bind to normal tissues, but they were observed to bind to cholangiocarcinoma tissues (FIG. 4).

This result accounts for the expression of L1CAM in cholangiocarcinoma tissues.

L1CAM expression was observed in 45.2% of 42 intrahepatic cholangiocarcinoma patients and 39.8% of 103 extrahepatic cholangiocarcinoma patients, as analyzed by immunohistochemical staining using the A10-A3 antibody (FIG. 5). Particularly, L1CAM is expressed at a high level in the invasive front, which explains the metastasis initiation of cholangiocarcinoma (FIG. 4).

Example 6

Statistical Analysis for the Expression Rate of L1CAM in Cholangiocarcinoma and the Survival Rate of Cholangiocarcinoma Patients The correlation between L1CAM expression rate and survival rate was analyzed in patients suffering from extrahepatic cholangiocarcinoma (60 cases). Patient groups showing high L1CAM expression rates were found to decrease with statistical significance in overall survival (OS) and disease free survival (DFS), that is, to increase in death risk, compared to those with low L1CAM expression rates (FIG. 6). As seen in the survival graph, there are great differences and statistical significance in 2-year OS between cholangiocarcinoma patients exhibiting high and low L1CAM expression rates. Also, the 2-year DFS of cholangiocarcinoma patients with low L1CAM expression rates was different with statistical significance from that of cholangiocarcinoma patients with high L1CAM expression rates.

In contrast, there is no statistical significance in the correlation between the survival of patients and the expression rate of EGFR (epidermal growth factor receptor), known to be overexpressed in cholangiocarcinoma or other tumors (FIG. 6). These results imply that antibodies to L1CAM are useful for the diagnosis and treatment of cholangiocarcinoma and can be applied to the early diagnosis of the metastasis of cholangiocarcinoma, thereby increasing the therapeutic effect thereof on the disease. It is apparent from the data of the statistical analysis for correlation between L1CAM expression rate and survival that higher mortality occurs in cholangiocarcinoma patients with high L1CAM expression rates than those with low L1CAM expression rates.

Demonstrating that L1CAM is a poor prognostic factor, the results indicate that L1CAM may be a target for the treatment of cholangiocarcinoma. Although expressed at a high level in cholangiocarcinoma, in contrast, EGFR, which had been used as a target of therapeutic agents for current clinical use in the treatment of colon cancer (e.g., cetuximab, chimeric antibody to EGFR), was proven not to be a poor prognostic factor for cholangiocarcinoma, as deduced from the correlation between EGFR expression rates and survival rates. This is proof that not all of the molecules which are overexpressed in cancer are poor prognostic factors for cancer and thus important targets for the treatment thereof.

Example 7

Effect of the Suppression of L1CAM Expression on Cholangiocarcinoma Cells

Example 7-1

Inhibition of L1CAM Expression in Cholangiocarcinoma Cells Using siRNAs

L1CAM expression was knocked down in Choi-CK and SCK cells. To this end, the carcinoma cells were transfected with two siRNA oligonucleotides for L1CAM (5'-TGGTA-CAGTCTGGGdtdt-3'; SEQ ID NO: 1 and 5'-CAG-CAACTTTGCTCAGAGGdtdt-3'; SEQ ID NO: 2) or a non-specific oligonucleotide (5'-CAGTCGCGTTTGCGACTGGdtdt-3' (SEQ ID NO: 3), and cultured for 72 hrs. L1CAM knockdown was estimated by flow cytometry, RT-PCR and Western blotting using the A10-A3 antibody. As a result, compared to a control treated with the non-specific siRNA, Choi-CK and SCK cells treated with siRNAs were measured to decrease in the total expression of L1CAM and in cell surface L1CAM level (panel A, FIG. 7).

Example 7-2

Evaluation of Activity of Cholangiocarcinoma Cells after Treatment with siRNA Against L1CAM Cell proliferation, invasion and migration were compared between cholangiocarcinoma cells transfected with the siRNA against L1CAM and with the non-specific siRNA. The degree of proliferation was estimated by counting the number of cells with the aid of Tryphan Blue 72 hours after culturing the same number of cells. The degrees of invasion and migration were analyzed using a QCM 24-well cell invasion assay kit (Chemicon) and a QCM 24-well colorimetric cell migration assay kit (Chemicon), respectively. Carcinoma cells, in which L1CAM was knocked down by siRNA, displayed a decreased degree of proliferation, invasion and migration compared to carcinoma cells expressing L1CAM at normal levels. These results indicate that L1CAM plays a role in the growth, migration and invasion of cholangiocarcinoma cells (panel B, FIG. 7).

Example 8

Inhibition of L1CAM-Specific Antibody Against Growth of Cholangiocarcinoma Cells Anti-L1CAM antibodies were evaluated for their inhibitory effects on the growth of cholangiocarcinoma cells. Choi-CK and SCK cells, to which the A10-A3 antibody binds, were used in this test while an ovarian carcinoma cell line (SK-OV-3) and ACNH served as a positive control and a negative control, respectively. These cells were seeded at a density of $2\times10^5$ cells/well in 24-well plates containing 3 ml of a medium per well, and cultured. The monoclonal antibody was added to each well at a concentration of 10 µg/ml before the cells were incubated in an incubator at 37° C. for 10 days. After being collected, the cells, alive and dead, were counted using 0.2% Tryphan Blue and the survival rates of the cells were expressed as percentages of total cell number. When treated with the A10-A3 antibody, Choi-CK and SCK cells grew at a distinctively decreased rate, like SK-OV3 cells, but ACHN cells proliferated normally (panel A, FIG. 8). On the other hand, 4-63 antibody was found to inhibit the growth of cholangiocarcinoma cells (panel B, FIG. 8).

Upon the treatment of cholangiocarcinoma cells therewith, UJ127 (Chemicon) antibody, known to specifically bind to L1CAM, inhibited the growth of the cancer cells significantly. In the case of 5G3 (Pharmingen), which also specifically binds to L1CAM, however, the growth of the cholangiocarcinoma cell (Choi-CK) was inhibited only slightly (panel C, FIG. 8). The 5G3 antibody was found to bind to the Choi-SK cell (panel C, FIG. 1). These results indicate that the binding of anti-L1CAM antibodies to tumor cells does not always inhibit the growth of tumor cells.

Example 9

Inhibitory Effects of L1CAM-Specific Antibodies on Invasion and Migration of Cholangiocarcinoma Cells A cell invasion assay was carried out using a QCM 24-well cell invasion assay kit (CHEMICON). The ECM layer of each insert was rehydrated with 300 µl of pre-warmed serum-free media (RPMI, 10 mM HEPES, pH 7.4) at room temperature for 30 min. Choi-CK, SCK, SK-OV3, and ACHN cells were washed twice with PBS and treated with 3 ml of trypsin-EDTA in an incubator at 37° C. The detached cells were harvested and adjusted to a density of $1\times10^5$ cells in 200 µl of invasion medium (RPMI, 10 mM HEPES, pH 7.4, 0.5% BSA). The cells were then inserted into each insert and incubated with the A10-A3 antibody, 4-63 antibody, 5G3 antibody (10 µg/ml) and normal mouse IgG (10 µg/ml). The lower chamber was filled with an invasion medium supplemented with 10% FBS, and incubated in an incubator at 37° C. for 72 hrs. Afterwards, the cells and medium remaining in each insert were removed, and each insert was transferred to a new well. Each insert was placed in 225 µl of pre-warmed cell detachment solution, and incubated in an incubator at 37° C. for 30 min. The insert was shaken to completely detach the remaining cells, and 75 µl of lysis buffer/dye solution was added to each well containing cells and the cell detachment solution, followed by incubation at room temperature for 15 min. 200 µl of the mixture was transferred to a 96-well plate, and fluorescence was read at 480/520 nm. The A10-A3 antibody was found to inhibit the cell invasion of Choi-SK, SCK and SK-OV3, but not to induce inhibition of the cell invasion (panel A, FIG. 9). Also, the 4-63 antibody reduced the invasion of Choi-SK cells (panel A, FIG. 9). The 5G3 antibody inhibited the invasion of Choi-SK cells less efficiently than did the A10-A3 and 4-63 antibodies (panel A, FIG. 7).

A cell migration assay was conducted in the same procedure as described above, with the exception that collagen type I was layered at a concentration of 10 g/ml on the bottom of the insert. The A10-A3 antibody was observed to inhibit the cell migration of Choi-SK, SCK and SK-OV-3, but not to inhibit the cell migration of ACHN (FIG. 9). Also, the antibodies inhibited the migration of Choi-SK, SCK and SK-OV-3 (FIG. 9).

Example 10

Inhibitory Effect of A10-A3 Antibody on Signal Transduction in Cancer Cells

Example 10-1

Inhibition of A10-A3 Antibody Against the PCNA Expression of Cancer Cell

Western blotting was performed to examine whether the proliferating cell nuclear antigen (PCNA) expression, accounting for cell proliferation, was inhibited by the A10-A3 antibody. In this regard, Choi-SK cells were incubated for 72 hours with A10-A3 or IgG 10, collected, and dissolved in a cell lysis buffer. Protein concentration was determined using a BCA (bicinchoninic acid) protein assay kit (Pierce). 40 μg of the protein was run on 8% SDS-PAGE and transferred onto a nitrocellulose membrane at 25 V for 90 min. The blots were blocked overnight at 4° C. in 5% skim milk and incubated for 1 hour with mouse monoclonal anti-PCNA (Novocastra Laboratories 1:500) antibody and anti-β actin (Oncogene, 1:4000) antibody. Then, the membrane was treated with anti-mouse horseradish peroxidase-conjugated antibody (Cell Signaling, 1:1000) and washed with PBST before visualizing PCNA and β-actin with an enhanced chemiluminescence reagent (ECL) (Amersham Pharmacia Biotech). Significantly reduced expression of PCNA was observed only in the Choi-SK cells treated with the A10-A3 antibody.

Example 10-2

Inhibition of PCNA Expression ERK Phosphorylation

Western blotting was performed to determine whether the A10-A3 antibody decreases mitogen-activated protein kinase (MAPK), which is involved in the growth, migration and survival of tumor cells. Choi-SK cells were incubated with 10 μg/ml of A10-A3 antibody or mouse IgG for 72 hours, harvested, and lysed with cell lysis buffer. Protein concentrations were determined using a bicinchoninic acid (BCA) protein assay kit (Pierce), and 40 μg of proteins were run on 12% SDS-PAGE. The proteins were transferred onto a nitrocellulose membrane at 25 V for 90 min. The blots were blocked with 5% skim milk at 4° C. overnight, and incubated overnight with rabbit polyclonal anti-phospho MAPK antibody (Ab cam, diluted 1:1000) in 1% skim milk. The same amount of proteins was treated according to the same procedure described above in order to investigate the expression of non-phosphorylated MAPK, and the blocked nitrocellulose membrane was incubated with anti-MAPK antibody (Ab cam, diluted 1:1000) for 1 hr. The blots were incubated with anti-rabbit HRP-conjugated antibody (Cell Signaling, diluted 1:10000) for 1 hr. After the blots were washed with PBST, phospho-MAPK and MAPK were detected using ECL (Amersham Pharmacia Biotech). Among the Choi-CK cells expressing the same MAPK, only those treated with the A10-A3 antibody remarkably decreased in phospho-MAPK level (FIG. 10A).

Example 10-3

Inhibition of AKT Phosphorylation by A10-A3 Antibody

Western blotting was performed in order to determine whether the A10-A3 antibody decreases AKT phosphorylation, which is involved in the survival of tumor cells. Choi-CK cells were incubated with 10 μg/ml of A10-A3 or mouse IgG for 1, 1.5 and 2 hours, harvested and lysed with cell lysis buffer. Protein concentrations were determined using a BCA protein assay kit (Pierce), and 40 μg of the proteins were run on 12% SDS-PAGE. The proteins were transferred onto a nitrocellulose membrane at 25 V for 90 min. The blots thus formed were blocked with 5% skim milk at 4° C. overnight, and incubated overnight with rabbit polyclonal anti-phospho Akt antibody (Ab cam, 1:1000 diluted) and rabbit polyclonal anti-Akt (Abcam, 1:1000 diluted) in 1% skim milk, followed by reaction with anti-rabbit IgG HRP (Santa Cruz 1:1000 diluted) for 1 hour. After the blots were washed with PBST, phospho-Akt and total Akt were detected using ECL (Amersham Pharmacia Biotech). Phospho-Akt levels remarkably decreased only in A10-A3 antibody-treated Choi-CK cells (FIG. 10B).

Example 10-4

Inhibition of FAK Activation by A10-A3 Antibody

Western blotting was performed to determine whether the A10-A3 antibody decreases focal adhesion kinase (FAK) phosphorylation, which plays an important role in the growth and migration of tumor cells. Choi-CK and SCK cells were incubated with 10 μg/ml of A10-A3 antibody for 0.5, 1, 1.5 and 2 hours, harvested and lysed with cell lysis buffer. Protein concentrations were determined using a BCA protein assay kit (Pierce), and 40 μg of proteins were run on 7.5% SDS-PAGE. The proteins were transferred onto a nitrocellulose membrane at 25 V for 90 min. The blots thus formed were blocked with 5% skim milk at 4° C. overnight, and incubated overnight with rabbit polyclonal anti-phospho FAK antibody (Ab cam, 1:1000 diluted) in 1% skim milk and then with anti-β-actin (Oncogene, 1:4000 diluted) for 1 hr. The blots were then incubated with anti-rabbit HRP-conjugated antibody (Cell Spring, 1:10000 diluted) for 1 hr. After the blot was washed with TBST, phospho-FAK and β-actin levels were detected using enhanced chemiluminescence reagent (ECL) (Amersham Pharmacia Biotech). Both of the Choi-CK and SCK cells treated with the A10-A3. antibody were observed to decrease in phospho-FAK level (FIG. 10C).

Example 11

Assay of A10-A3 Antibody for Inhibitory Activity Against Cancer Cells in Mouse Model Nude mice Balb/c nu/nu which were 6~8 weeks old and weighed 18~22 g were purchased via Central Lab. Animal Inc. from Japan SLC and acclimated for one week in a lab of the Korean Research Institute of Bioscience and Biotechnology. Choi-CK cells ($3 \times 10^6$) were subcutaneously transplanted into the mice and were grown to a tumor mass having a size of 390 mm$^3$ on Day 20 (FIG. 10A). The tumor volume was assessed according to the formula V=long axis (mm)× short axis mm)×height (mm)×½. On the final day, the mice were sacrificed with $CO_2$ gas and the tumors were separated and weighed. The body weights of the mice were also measured to determine toxicity. Standard deviations (SDs) and p values were evaluated using ANOVA (Prism, GraphPad Software, USA) and students t-test.

When the A10-A3 antibody was injected at a dose of 10 mg/kg into a tail vein three times a week from day 1, potent anticancer effects were observed until Day 20 (panel A, FIG. 1). Mouse IgG antibody was injected at the same dose as a control. The standard tumor volume was measured to be 232 mm$^3$, which accounted for the anticancer activity about 40% higher than the control (FIG. 11A). On the final day (Day 20), the tumors were separated and weighed (Panel B, FIG. 11). The standard tumor weights of the control and the A10-A3-administered group were 872 mg and 516 mg, respectively, which accounted for the fact that the anticancer activity of the A10-A3 antibody was 40% higher than that of the control.

The nude mice were monitored for body weight for 20 days in order to predict the toxicity of A10-A3. Also, the behavior of the mice was observed with the naked eye (panel D, FIG.

11). Compared to the control on Day 20, the mice treated with the antibody of interest were observed to undergo neither body weight changes nor abnormal behaviors.

INDUSTRIAL APPLICABILITY

As described hitherto, it is first discovered in the present invention that L1CAM is expressed on the cell surface of cholangiocarcinoma to play an important role in the growth and invasion of cancer and is a poor prognostic factor for cholangiocarcinoma. Therefore, antibodies, binding to the L1CAM protein on the cholangiocarcinoma cell surface or siRNAs, antisense oligonucleotides or shRNAs, suppressing L1CAM expression in cholangiocarcinoma cells, and a pharmaceutical composition comprising the same according to the present invention can be applied to the treatment of cholangiocarcinoma because they are proven to inhibit the growth, invasion and migration of cholangiocarcinoma.

What is claimed is:

1. A method of treating cholangiocarcinoma, the method comprising:
   administering, to a patient in need of treating cholangiocarcinoma, a pharmaceutical composition comprising an inhibitor of an L1CAM activity that is selected from the group consisting of an anti-L1CAM antibody and antigen binding fragments of the anti-L1CAM antibody.

2. A method of inhibiting growth or metastasis of cholangiocarcinoma, the method comprising:
   administering, to a person in need of inhibiting growth or metastasis of cholangiocarcinoma, a pharmaceutical composition comprising an inhibitor of an L1CAM activity that is selected from the group consisting of an anti-L1CAM antibody and antigen binding fragments of the anti-L1CAM antibody.

3. The method according to claim 1, wherein the anti-L1CAM antibody comprises at least one selected from the group consisting of:
   UJ127;
   4-63 secreted from a hybridoma deposited with Accession Number KCTC 10966BP; and
   A10-A3 secreted from a hybridoma deposited with Accession Number KCTC 10909BP.

4. The method according to claim 2, wherein the anti-L1CAM antibody comprises at least one selected from the group consisting of:
   UJ127;
   4-63 secreted from a hybridoma deposited with Accession Number KCTC 10966BP; and
   A10-A3 secreted from a hybridoma deposited with Accession Number KCTC 10909BP.

* * * * *

SEQUENCE LISTING

```
<160> NUMBER OF SEQ ID NOS: 13

<210> SEQ ID NO 1
<211> LENGTH: 16
<212> TYPE: DNA
<213> ORGANISM: Artificial Sequence
<220> FEATURE:
<223> OTHER INFORMATION: siRNA for L1CAM
<220> FEATURE:
<221> NAME/KEY: misc_feature
<222> LOCATION: (15)..(16)
<223> OTHER INFORMATION: n is 3' dt, whcih is attached oligo dt for RNA
      identification

<400> SEQUENCE: 1
tggtacagtc tgggnn                                                    16

<210> SEQ ID NO 2
<211> LENGTH: 21
<212> TYPE: DNA
<213> ORGANISM: Artificial Sequence
<220> FEATURE:
<223> OTHER INFORMATION: siRNA for L1CAM
<220> FEATURE:
<221> NAME/KEY: misc_feature
<222> LOCATION: (20)..(21)
<223> OTHER INFORMATION: n is 3' dt, whcih is attached oligo dt for RNA
      identification

<400> SEQUENCE: 2
cagcaacttt gctcagaggn n                                              21

<210> SEQ ID NO 3
<211> LENGTH: 21
<212> TYPE: DNA
<213> ORGANISM: Artificial Sequence
<220> FEATURE:
<223> OTHER INFORMATION: Non specific oligonucleotide for L1CAM
<220> FEATURE:
<221> NAME/KEY: misc_feature
<222> LOCATION: (20)..(21)
<223> OTHER INFORMATION: n is 3' dt, whcih is attached oligo dt for RNA
      identification

<400> SEQUENCE: 3
cagtcgcgtt tgcgactggn n                                              21

<210> SEQ ID NO 4
<211> LENGTH: 10
<212> TYPE: PRT
<213> ORGANISM: Artificial Sequence
<220> FEATURE:
<223> OTHER INFORMATION: Artificial Sequence based on human L1CAM
      protein fragment

<400> SEQUENCE: 4

Asp Leu Gln Glu Leu Gly Asp Ser Asp Lys
 1               5                  10
```

-continued

```
<210> SEQ ID NO 5
<211> LENGTH: 15
<212> TYPE: PRT
<213> ORGANISM: Artificial Sequence
<220> FEATURE:
<223> OTHER INFORMATION: Artificial Sequence based on human L1CAM
      protein fragment

<400> SEQUENCE: 5

Leu Val Leu Ser Asp Leu His Leu Leu Thr Gln Ser Gln Val Arg
  1               5                  10                  15

<210> SEQ ID NO 6
<211> LENGTH: 14
<212> TYPE: PRT
<213> ORGANISM: Artificial Sequence
<220> FEATURE:
<223> OTHER INFORMATION: Artificial Sequence based on human L1CAM
      protein fragment

<400> SEQUENCE: 6

Tyr Asp Ile Glu Phe Glu Asp Lys Glu Met Arg Pro Glu Lys
  1               5                  10

<210> SEQ ID NO 7
<211> LENGTH: 12
<212> TYPE: PRT
<213> ORGANISM: Artificial Sequence
<220> FEATURE:
<223> OTHER INFORMATION: Artificial Sequence based on human L1CAM
      protein fragment

<400> SEQUENCE: 7

Leu Val Val Phe Pro Thr Asp Asp Ile Ser Leu Lys
  1               5                  10

<210> SEQ ID NO 8
<211> LENGTH: 14
<212> TYPE: PRT
<213> ORGANISM: Artificial Sequence
<220> FEATURE:
<223> OTHER INFORMATION: Artificial Sequence based on human L1CAM
      protein fragment

<400> SEQUENCE: 8

Ala Gln Leu Leu Val Val Gly Ser Pro Cys Pro Val Pro Arg
  1               5                  10

<210> SEQ ID NO 9
<211> LENGTH: 22
<212> TYPE: PRT
<213> ORGANISM: Artificial Sequence
<220> FEATURE:
<223> OTHER INFORMATION: Artificial Sequence based on human L1CAM
      protein fragment

<400> SEQUENCE: 9

Tyr Gly Pro Gly Glu Pro Ser Pro Val Ser Glu Thr Val Val Thr Pro
  1               5                  10                  15

Glu Ala Ala Pro Glu Lys
             20

<210> SEQ ID NO 10
<211> LENGTH: 24
<212> TYPE: PRT
<213> ORGANISM: Artificial Sequence
<220> FEATURE:
<223> OTHER INFORMATION: Artificial Sequence based on human L1CAM
      protein fragment
```

```
<400> SEQUENCE: 10

Ala Phe Gly Ala Pro Val Pro Ser Val Gln Trp Leu Asp Glu Asp Cys
 1               5                  10                  15

Thr Thr Val Leu Gln Asp Lys Arg
             20

<210> SEQ ID NO 11
<211> LENGTH: 1257
<212> TYPE: PRT
<213> ORGANISM: Homo sapiens

<400> SEQUENCE: 11

Met Val Val Ala Leu Arg Tyr Val Trp Pro Leu Leu Leu Cys Ser Pro
 1               5                  10                  15

Cys Leu Leu Ile Val Ile Pro Glu Glu Tyr Glu Gly His His Val Met
             20                  25                  30

Glu Pro Pro Val Ile Thr Glu Gln Ser Pro Arg Arg Leu Val Val Phe
         35                  40                  45

Pro Thr Asp Asp Ile Ser Leu Lys Cys Glu Ala Ser Gly Lys Pro Glu
 50                  55                  60

Val Gln Phe Arg Trp Thr Arg Asp Gly Val His Phe Lys Pro Lys Glu
 65                  70                  75                  80

Glu Leu Gly Val Thr Val Tyr Gln Ser Pro His Ser Gly Ser Phe Thr
                 85                  90                  95

Ile Thr Gly Asn Asn Ser Asn Phe Ala Gln Arg Phe Gln Cys Ile Tyr
             100                 105                 110

Arg Cys Phe Ala Ser Asn Lys Leu Gly Thr Ala Met Ser His Glu Ile
         115                 120                 125

Arg Leu Met Ala Glu Gly Ala Pro Lys Trp Pro Lys Glu Thr Val Lys
 130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                 165                 170                 175

Leu His Ile Lys Gln Asp Glu Arg Val Ile Met Gly Gln Asn Gly Asn
             180                 185                 190

Leu Tyr Phe Ala His Val Leu Thr Ser Asp His His Ser Asp Tyr Ile
         195                 200                 205

Cys His Ala His Phe Pro Gly Thr Arg Thr Ile Ile Gln Lys Glu Pro
 210                 215                 220

Ile Asp Leu Arg Val Lys Ala Thr Asn Ser Asn Ile Asp Arg Lys Pro
225                 230                 235                 240

Arg Leu Leu Phe Pro Tyr Asn Ser Ser His Leu Val Ala Leu Gln
                 245                 250                 255

Gly Gln Pro Leu Val Leu Glu Cys Ile Ala Glu Gly Phe Pro Ile Pro
             260                 265                 270

Thr Ile Lys Trp Leu Arg Pro Ser Gly Pro Met Pro Ala Asp Arg Val
         275                 280                 285

Thr Tyr Gln His His Met Lys Thr Leu Gln Leu Leu Lys Val Gly Glu
 290                 295                 300

Glu Asp Asp Gly Glu Tyr Arg Cys Leu Ala Glu Asn Ser Leu Gly Ser
305                 310                 315                 320

Ala Arg His Ala Tyr Tyr Val Thr Val Glu Ala Ala Pro Tyr Trp Leu
                 325                 330                 335
```

-continued

```
His Lys Pro Gln Ser His Leu Tyr Gly Pro Gly Glu Leu Ala Arg Leu
            340                 345                 350

Asp Cys Gln Val Gln Gly Arg Pro Gln Pro Glu Val Ile Trp Arg Ile
            355                 360                 365

Asn Gly Ile Pro Val Glu Glu Leu Ala Lys Asp Gln Lys Tyr Arg Ile
            370                 375                 380

Gln Arg Gly Ala Leu Ile Leu Ser Asn Val Gln Pro Ser Asp Ile Met
385                 390                 395                 400

Val Ile Gln Cys Glu Ala Arg Asn His Gly Leu Leu Leu Ala His
            405                 410                 415

Ala Tyr Ile Tyr Val Val Gln Leu Pro Ala Lys Ile Leu Thr Ala Asp
            420                 425                 430

Asn Gln Thr Tyr Met Ala Val Gln Gly Ser Thr Ala Tyr Leu Leu Cys
            435                 440                 445

Lys Ala Phe Gly Ala Pro Val Pro Ser Val Gln Trp Leu Asp Glu Asp
            450                 455                 460

Gly Thr Thr Val Leu Gln Asp Glu Arg Phe Phe Pro Tyr Ala Asn Gly
465                 470                 475                 480

Thr Leu Gly Ile Arg Asp Leu Gln Ala Asn Asp Thr Gly Arg Tyr Phe
            485                 490                 495

Cys Leu Ala Ala Asn Asp Gln His His Val Thr Thr Asn Ala His Leu
            500                 505                 510

Lys Val Lys Asp Ala Thr Gln Thr Thr Gln Gly Pro Arg Ser Thr Ile
            515                 520                 525

Glu Lys Lys Gly Ser Arg Val Thr Phe Thr Cys Gln Ala Ser Phe Asp
            530                 535                 540

Pro Ser Leu Gln Pro Ser Ile Thr Trp Arg Gly Asp Gly Arg Asp Ile
545                 550                 555                 560

Gln Glu Leu Gly Asp Ser Asp Lys Tyr Phe Ile Glu Asp Gly Arg Leu
            565                 570                 575

Val Ile His Ser Leu Asp Tyr Ser Asp Gln Gly Asn Tyr Ser Cys Val
            580                 585                 590

Ala Ser Thr Glu Leu Asp Val Val Glu Ser Arg Ala Gln Leu Leu Val
            595                 600                 605

Val Gly Ser Pro Gly Pro Val Pro Arg Leu Val Leu Ser Asp Leu His
            610                 615                 620

Leu Leu Thr Gln Ser Gln Val Arg Val Ser Trp Ser Pro Ala Glu Asp
625                 630                 635                 640

His Asn Ala Pro Ile Glu Lys Tyr Asp Ile Glu Phe Glu Asp Lys Glu
            645                 650                 655

Met Ala Pro Glu Lys Trp Tyr Ser Leu Gly Lys Val Pro Gly Asn Gln
            660                 665                 670

Thr Ser Thr Thr Leu Lys Leu Ser Pro Tyr Val His Tyr Thr Phe Arg
            675                 680                 685

Val Thr Ala Thr Asn Lys Tyr Gly Pro Gly Glu Pro Ser Pro Val Ser
            690                 695                 700

Glu Thr Val Val Ile Pro Glu Ala Ala Pro Glu Lys Asn Pro Val Asp
705                 710                 715                 720

Val Lys Gly Glu Gly Asn Glu Thr Thr Asn His Val Ile Thr Trp Lys
            725                 730                 735

Pro Leu Arg Trp Met Asp Trp His Ala Pro Gln Val Gln Tyr Arg Val
            740                 745                 750

Gln Trp Arg Pro Gln Gly Thr Arg Gly Pro Trp Gln Glu Gln Thr Val
            755                 760                 765
```

```
Ser Asp Pro Phe Leu Val Val Ser His Thr Ser Thr Phe Val Pro Tyr
    770                 775                 780

Glu Thr Lys Val Gln Ala Val Asn Ser Gln Gly Lys Gly Pro Glu Pro
785                 790                 795                 800

Gln Val Thr Ile Gly Tyr Ser Gly Glu Asp Tyr Pro Gln Ala Thr Pro
                805                 810                 815

Glu Leu Glu Gly Thr Glu Thr Leu Asn Ser Ser Ala Val Leu Val Lys
            820                 825                 830

Trp Arg Pro Val Asp Leu Ala Gln Val Lys Gly His Leu Arg Gly Tyr
        835                 840                 845

Asn Val Thr Tyr Trp Arg Glu Gly Ser Gln Arg Lys His Ser Lys Arg
    850                 855                 860

His Ile His Lys Asp His Val Val Pro Ala Asn Thr Thr Ser Val
865                 870                 875                 880

Thr Leu Ser Gly Leu Arg Pro Tyr Ser Tyr His Leu Glu Val Gln
                885                 890                 895

Ala Phe Asn Gly Arg Gln Ser Gly Pro Ala Ser Glu Phe Thr Phe Ser
                900                 905                 910

Thr Pro Glu Gly Val Pro Gly His Pro Glu Ala Leu His Leu Asx Cys
            915                 920                 925

Gln Ser Asn Thr Ser Leu Leu Leu Arg Trp Gln Pro Pro Leu Ser His
    930                 935                 940

Asn Gly Val Leu Thr Gly Tyr Val Leu Ser Tyr His Pro Leu Asp Glu
945                 950                 955                 960

Gly Gly Lys Gly Gln Leu Ser Pro Asn Leu Arg Asp Pro Glu Leu Arg
                965                 970                 975

Thr His Asn Leu Leu Asp Leu Ser Pro His Leu Arg Tyr Arg Phe Gln
            980                 985                 990

Leu Gln Ala Thr Thr Lys Glu Gly Pro Gly Phe Ala Ile Val Arg Glu
        995                 1000                1005

Gly Gly Thr Asn Ala Leu Ser Gly Ile Ser Asp Pro Gly Asn Ile Ser
    1010                1015                1020

Ala Thr Ala Gly Glu Asn Tyr Ser Val Val Ser Trp Val Pro Lys Glu
1025                1030                1035                1040

Gly Gln Cys His Pro Arg Pro His Ile Leu Pro Lys Ala Leu Gly Glu
                1045                1050                1055

Glu Lys Gly Gly Ala Ser Leu Ser Pro Gln Tyr Val Ser Tyr Asn Gln
            1060                1065                1070

Ser Ser Tyr Thr Gln Trp Asp Leu Gln Pro Asp Ile Asp Tyr Glu Ile
        1075                1080                1085

His Leu Phe Lys Glu Arg Met Phe Arg His Gln Asn Ala Val Lys Thr
    1090                1095                1100

Asn Gly Thr Gly Arg Val Arg Leu Pro Pro Ala Gly Glu Ala Thr Glu
1105                1110                1115                1120

Gly Trp Pro Ile Gly Phe Val Ser Ala Ile Ile Leu Leu Leu Leu Val
                1125                1130                1135

Leu Leu Ile Leu Cys Phe Ile Lys Arg Ser Lys Gly Gly Lys Tyr Ser
            1140                1145                1150

Val Lys Asp Lys Glu Asp Thr Gln Val Asp Ser Glu Ala Arg Pro Met
        1155                1160                1165

Lys Asp Glu Thr Phe Gly Glu Tyr Arg Ser Leu Phe Ser Asp Asn Glu
    1170                1175                1180

Glu Lys Ala Pro Gly Ser Ser Gln Pro Ser Leu Asn Gly Asp Ile Lys
1185                1190                1195                1200
```

```
Pro Leu Gln Ser Asp Asp Ser Leu Ala Asp Tyr Gly Gly Ser Val Asp
                1205                1210                1215

Val Gln Phe Asn Glu Asp Gly Ser Pro Ile Gly Gln Tyr Ser Gly Lys
            1220                1225                1230

Lys Arg Lys Arg Ala Ala Gly Gly Asn Asp Ser Ser Gly Ala Thr Ser
        1235                1240                1245

Pro Ile Asn Pro Ala Val Ala Leu Glu
    1250                1255

<210> SEQ ID NO 12
<211> LENGTH: 38
<212> TYPE: DNA
<213> ORGANISM: Artificial Sequence
<220> FEATURE:
<223> OTHER INFORMATION: primer for Ig-dom-F

<400> SEQUENCE: 12
gaggaggaat tccggcgccg ggaaagatgg tcgtggcg                          38

<210> SEQ ID NO 13
<211> LENGTH: 34
<212> TYPE: DNA
<213> ORGANISM: Artificial Sequence
<220> FEATURE:
<223> OTHER INFORMATION: primer for L1-Fn-Stop-R

<400> SEQUENCE: 13
ctctagagtt ctcgagtcag agcctcacgc ggcc                              34
```